(12) United States Patent
Lary et al.

(10) Patent No.: US 6,941,005 B2
(45) Date of Patent: Sep. 6, 2005

(54) MONITORING AND CONTROL OF DROPLET SORTING

(75) Inventors: Todd P. Lary, Homestead, FL (US); Christopher W. Snow, Homestead, FL (US); John S. Riley, Miami, FL (US); Robert C. Burr, Miami, FL (US)

(73) Assignee: Coulter International Corp., Miami, FL (US)

( * ) Notice: Subject to any disclaimer, the term of this patent is extended or adjusted under 35 U.S.C. 154(b) by 5 days.

(21) Appl. No.: 10/286,499

(22) Filed: Nov. 1, 2002

(65) Prior Publication Data

US 2004/0086159 A1 May 6, 2004

(51) Int. Cl.[7] ............................. G06K 9/00; G01N 35/02; G01J 3/30
(52) U.S. Cl. ......................... 382/133; 382/170; 436/50; 356/317
(58) Field of Search ............................ 382/128, 129, 382/133, 134, 168, 169, 170, 171, 172, 274, 275; 356/23, 70, 317; 436/8, 18, 23, 50, 63, 164; 702/21

(56) References Cited

U.S. PATENT DOCUMENTS

| | | | |
|---|---|---|---|
| 3,705,383 A | * 12/1972 | Frayer | .................. 382/134 |
| 3,710,933 A | 1/1973 | Fulwyler et al. | |
| 3,962,125 A | 6/1976 | Armstrong | |
| 4,361,400 A | 11/1982 | Gray et al. | |
| 4,981,580 A | 1/1991 | Auer | |
| 5,422,712 A | * 6/1995 | Ogino | .................. 356/73 |
| 5,483,469 A | 1/1996 | Van den Engh et al. | |
| 5,602,039 A | 2/1997 | Van den Engh | |
| 5,627,908 A | * 5/1997 | Lee et al. | .................. 382/133 |
| 5,700,692 A | 12/1997 | Sweet | |
| 5,856,665 A | * 1/1999 | Price et al. | .................. 250/205 |
| 5,916,449 A | 6/1999 | Ellwart et al. | |
| 6,079,836 A | 6/2000 | Burr et al. | |
| 6,248,590 B1 | 6/2001 | Malachowski | |
| 6,813,017 B1 | * 11/2004 | Hoffman et al. | .................. 356/317 |

OTHER PUBLICATIONS

Lindmo, T., et al, "Flow Sorters for Biological Cells", *Flow Cytometry and Sorting*, 2nd ed., Wiley–Liss, Inc., pp. 145–169 (1990).

* cited by examiner

Primary Examiner—Mehrdad Dastouri
(74) Attorney, Agent, or Firm—Howson and Howson; Mitchell E. Alter

(57) ABSTRACT

Methods, systems and apparatus are provided for sorting particles in a stream of a sample in a flow cytometer by producing from a stable sort having desirable sort characteristics multiple images of a portion of the stream; generating from the multiple images an averaged numerical reference standard representative of the stable sort; continuously collecting during the sorting multiple running images of the portion of the stream; generating from the multiple running images at least one numerical sample average representative of the sample sort of each collection of the multiple running images; and comparing each numerical sample average to the numerical reference standard and determining whether a sample average exhibits a deviation from the reference standard that requires an adjustment of the sort. The sort may then be adjusted to eliminate or reduce the deviation and maintain the stable sort of the reference histogram. A novel imaging apparatus may be employed in a flow cytometer performing this method.

57 Claims, 10 Drawing Sheets

MONITORING AND CONTROL OF DROPLET SORTING

BACKGROUND OF THE INVENTION

This invention relates in general to the field of flow cytometer systems for studying characteristics of a stream, including particles entrained in droplets of a stream, and particularly for monitoring and controlling droplet sorting and specifically droplet generation. The sorting of biological cells entrained in streams and the droplets thereof provides relatively pure samples for both biomedical research and clinical medicine. Various techniques of sorting cells using flow cytometry have been employed over the last two decades. See, e.g., Lindmo et al., "Flow Sorters for Biological Cells" in Flow Cytometry and Sorting, $2^{nd}$ ed. Wiley-Liss, Inc.: New York, 1990, pages 145–169; and U.S. Pat. Nos. 3,710,933; 4,361,400; 4,981,580; 5,483,469; and 5,602,039, among others.

Techniques used for cell sorting include flow sorters, such as flow cytometers. Conventional flow cytometers, such as illustrated in FIG. 1 of U.S. Pat. No. 6,079,836, include apparatus for generating a flow of a fluid consisting of small amounts of sample (which may be dye-treated) in a sheath fluid. Generally, the sheath fluid and its entrained sample are hydrodynamically focused and exit a nozzle, thereby forming a jet stream. A droplet generator in the cytometer generates droplets from the stream, such as by causing the jet to oscillate, thereby forming individual droplets for sorting. Additionally, conventional cytometers contain an apparatus for charging the jet to enable deflection of the droplets. See, e.g., U.S. Pat. Nos. 5,602,039 and 5,483,496. The cytometers also contain a device for deflecting the droplets and creating post-deflection trajectories of the droplets that are a function of the charge. Additionally, such conventional cytometers contain a collection apparatus for collecting the droplets having common post-deflection trajectories.

A crucial component of such cytometers and the systems by which they operate are the components that enable detection and imaging of characteristics of the stream, and particularly the droplets. For example, light beams or lasers can be directed at the sheath and sample stream, which can include the droplets, to excite and fluoresce dyes in the stream. Various parameters, such as forward and side light scatter, and fluorescent wavelengths of light are detected to identify sample particles in the stream and to sort specific droplets to obtain samples of the particles therein. Still other cytometers contain standard video cameras and standard video capture systems, such as charge coupled device (CCD) cameras, and other video apparatus to capture images of the stream and droplets.

Such conventional flow cytometers consist of either an electrostatic sorting system or a fluidic sorting system that is used to sort the particles. The electrostatic system enables control of certain sorting parameters by the system operator. The electrostatic sorting parameters that the operator controls include droplet charge, crystal frequency, crystal drive amplitude, sheath pressure and sample pressure.

Typically, sorting of the droplets containing the sample particles is accomplished over an extended period of time during which environmental changes can adversely influence the performance of an electrostatic sorter. Such environmental changes include temperature, acoustic vibrations, and atmospheric pressure. One or more of these environmental changes continually affects the sort, requiring the operator of the system to adjust the instrument during sorting to avoid contamination of the sort. To keep sort efficiency high, operators trained in the adjustment of the instrument must monitor the appearance of the jetting stream, and manually correct for any changes. It is both costly and tedious for an operator to be constantly monitoring these parameters and the sort performance.

Solutions of the prior art for improving the sort have included, among others, the use of a direct jet monitor, such as an optical monitor to illuminate the jet and the conditions within the jet through a charge coupled device (CCD) camera. Cytometers using this system provide an optical image of the actual droplet separation point and jet stream. Some optical monitoring systems are associated with a feedback system to automatically change the horizontal location of the jet or the point at which droplet separation occurs. See, e.g., U.S. Pat. No. 5,602,039. Still other cytometer systems examine the drop delay time based on a measurement of the speed of the fluid in the stream or determine the width of the stream correlative to the nozzle size used by the cytometer. See, e.g., U.S. Pat. No. 6,248,590.

Still other improved flow cytometers of the art excite the fluid jet by an acoustic vibration of 5 to 200 KHz, typically produced by a piezo crystal element, although any vibrating device can be used. This excitation can cause the jet stream to undulate and produce droplets at the rate of excitation. The phase of the undulations and the droplets produced, as well as the position of the undulations and droplets in reference to the jet stream nozzle are critical to the proper operation of these sorters. In order to automate control of the undulations and phase, images of the jetting stream are captured using a standard video camera and a standard video capture system.

However, an automation system utilizing video images and video processing requires that the jetting stream have sufficient contrast to be analyzed. Current imaging means produce an image with little contrast between the jetting stream and the light field behind the jetting stream. Other solutions in the art for improving sorting include the use of hardware such as image intensifiers and analog video processors to improve the contrast prior to digitization. However, the amount of contrast improvement is limited, and additional image manipulation can remove detail and alter the true image so that proper control is not ideal. See, e.g., U.S. Pat. No. 5,700,692.

Therefore, a need in the art exists for efficient methods, systems, and apparatus for maintaining a stable sorting system by establishing a stable sorting system and automatically adjusting sorting parameters of the sorting system. A need further exists for compositions and methods that allow the effects of the adjustments to be monitored and further allow that adjustment of these parameters to maintain a stable sorting system. Enhancements to flow cytometer apparatus and methods to enable contrast improvement and allow accurate characterization of particles in the droplet are also needed.

SUMMARY OF THE INVENTION

The present invention meets the needs of the art by providing, in one aspect, novel methods for sorting particles in a stream of a sample in a flow cytometer.

In one aspect, the method of the present invention involves producing from a stable sort having desirable sort characteristics a group of multiple images of a portion of the stream. Optionally these images are consecutive, and may further have background noises subtracted there from. From this group of multiple images an averaged numerical reference standard representative of the stable sort is generated. During the sorting, one or more groups of multiple running images of the same portion of the stream are continuously collected. Optionally these images are consecutive, and may further have background noises subtracted therefrom. From these multiple running images at least one numerical sample average representative of the sample sort of each group of the multiple running images is generated. Each numerical sample average is then compared to the numerical reference standard and a determination is made whether any numerical sample average exhibits a deviation from the reference standard that requires an adjustment of the sort. An additional aspect of such a method therefore can involve adjusting a processing condition of the sort in the cytometer as a function of the deviation. This method thereby minimizes the deviation in subsequently generated numerical sample averages and maintains the stable sort of the reference standard.

In another aspect, the present invention provides a novel sorting method as described above wherein each image of the stream is captured by positioning the stream between an image capturing device and a novel illumination field. The illumination field provides a light projecting area and an opaque masked area of a geometric pattern such that the pattern is imaged within the image of the stream taken by the image capturing device. In one contemplated embodiment, the masked area appears in the images as marking the outer edges of the stream, and the image capturing device has an angle of light acceptance sufficient to capture an image of the full width of the stream as well as light projecting from the illumination field along both lateral edges of the stream to provide a desired contrast between the stream and background of the image.

In yet another aspect, the invention provides a method for maintaining a stable sort of particles suspended in a sample comprising the following steps. The particles and a sheath fluid are serialized in a stream having a flow velocity in a conduit having an exit nozzle. Droplets are generated from the stream and have a common initial trajectory. Each of the droplets is formed from a corresponding jetting stream segment, that, when exiting the nozzle, contains a droplet-forming region. A time-varying electric field is applied to the stream so that the droplets are charged as a function of characterization of the contents of the corresponding stream segments. The droplets are thereafter deflected so that the post-deflection trajectories of the droplets are a function of the charges. The droplets having common post-deflection trajectories are collected. Utilizing these steps, multiple images of a portion of the stream are produced from a stable sort having desirable sort characteristics. Generally, the desirable characteristics are described by the operator of the method. From the multiple images is generated an averaged numerical reference standard representative of the stable sort.

Multiple running images of the portion of the stream are continuously collected during the sorting. At least one numerical sample average is generated from the multiple running images. This average is representative of the sample sort of each collection of the multiple running images, and is compared to the numerical reference standard. As described above, the method determines whether each numerical sample average exhibits a deviation from the reference standard, requiring an adjustment to the sort. If so, a processing condition of the sort in the cytometer is adjusted as a function of the deviation, to minimize the deviation in subsequent sample average values and maintain the stable sort of the reference standard.

In yet another aspect of this invention, a method for sorting particles in a stream of a sample in a flow cytometer comprises the following steps. A group of multiple images of a portion of the stream comprising the proximal point wherein the stream exits the nozzle of the cytometer to a distal point at which the contiguous stream transitions into individual droplets are produced from a stable sort having desirable sort characteristics. An averaged numerical reference standard representative of the stable sort is established therefrom. At least one, and preferably more groups of multiple running images of that portion of the stream are collected continuously during the sorting. From the multiple running images in each group, at least one numerical sample average is generated and is representative of the sample sort of each group. Each numerical sample average is compared to the numerical reference standard and a determination is made whether any sample average exhibits a deviation from the reference standard that requires an adjustment of the sort.

In still another aspect, the present invention provides a method for sorting particles in a stream of a sample in a flow cytometer that comprises the steps of the above-mentioned methods, with the additional step of selecting the numerical reference standard and the numerical sample average from among a number of specific numerical values generated from one or more histograms of the groups of multiple images. One numerical value is the averaged slope of the upstream edge of an undulation appearing downstream of the neck region of histograms generated from each group of multiple reference images or sample images. Another numerical value is the averaged slope of the downstream edge of the undulation appearing upstream of the neck region of these histograms. Still another numerical value is the average of the sum of the absolute values of the above mentioned slopes. Another useful value is the averaged midpoint of the segment defining the slope of the downstream undulation of the histograms. Still another numerical value is the averaged integral of the area of the histograms between the lower of the slope values of the above-mentioned upstream and downstream slopes.

In yet a further aspect, the invention provides a system for sorting particles in a stream of a sample in a flow cytometer. Components of this system include an imaging device for producing multiple images of a portion of the stream; an automated apparatus for generating from multiple images of a stable sort having desirable characteristics an averaged numerical reference standard representative of the stable sort; an automated means for continuously collecting during the sorting multiple running images of the portion of the stream and generating from the multiple running images at least one numerical sample average representative of the sample sort of each collection of the multiple running images; and an automated set-up for comparing each numerical sample average to the numerical reference standard and determining whether any of the sample averages exhibits a deviation from the reference standard requiring an adjustment to the sort.

In still a further aspect, the present invention provides an assembly for obtaining images of a fluid stream in a manner that produces dramatically enhanced contrast between the edges of the stream and the background captured within the image. The assembly includes an illumination field for illuminating the fluid stream from a side thereof. The illumination field provides a pattern of contrasting light and dark areas. An image capturing device is positioned relative to the fluid stream to obtain an image of at least a portion of the fluid stream that is backlit by the illumination field. The resulting image of the fluid stream includes an image of said pattern of contrasting light and dark areas as imaged within the fluid stream. Preferably, the illumination field comprises a light source and an opaque mask of a pre-determined pattern interposed between the light source and the fluid stream. For example, the pre-determined pattern may be a geometric pattern provided by a mask with an elongate slit, and the dark areas provided by the mask can mark the lateral edges of the fluid stream as captured in the image taken by the image capturing device. To this end, the image capturing device can have an angle of light acceptance that captures a full width of the fluid stream and light projecting from the light source adjacent and externally of the lateral edges of the fluid stream to provide the desired contrast. In addition, the geometric pattern of the mask can include at least one distinguishing mark that appears as a reference mark within the image of the fluid stream.

Other aspects and advantages of the present invention are described further in the following detailed description of the preferred embodiments thereof.

DESCRIPTION OF THE FIGURES

FIG. 2A is an image captured with no sheath fluid flow. FIG. 2B is an image with sheath flow. FIG. 2C shows the resultant image after taking the absolute value of a pixel by pixel subtraction of the images in 2A and 2B. FIG. 2D shows the resultant image after enhancing the image of FIG. 2C. FIG. 2E shows the image of FIG. 2D reduced to minimize the field of view, thereby increasing the resolution. FIG. 2F shows the image of FIG. 2E with the empty spaces in the jet filled in to allow creation of the desired histogram.

FIG. 4A illustrates an image and a histogram produced from averaging 10 such images of the jet showing the initial sort setup condition. The numerical standard calculated therefrom is the averaged midpoint of the segment of the slope downstream of the neck of the histogram. FIG. 4B is the image and histogram (based on 10 running sample images) of the jet. Comparison of the numerical sample midpoint average generated from this histogram with the reference standard demonstrated that the sort conditions have changed the sort jet and the stable sort is threatened. FIG. 4C is the histogram based on an average of 10 images taken of the jet after increasing the crystal drive. Calculation of the numerical sample midpoint average from this histogram and comparison with the reference standard demonstrates that the sort has stabilized.

FIG. 5A shows an image and histogram of the jet based on an average of 10 images, showing the initial stable sort setup condition. The numerical standard calculated therefrom is the averaged slope downstream of the neck of the histogram. FIG. 5B shows an image and histogram of the jet (based on 10 running sample images) after a temperature increase. Comparison of the numerical sample slope average generated from this histogram with the reference standard demonstrated that the sort conditions have changed the sort jet and the stable sort is threatened. A parameter of the stable sorting system requires adjustment. FIG. 5C shows an image and histogram based on an average of 10 images taken of the jet after a decrease in sheath pressure and crystal drive. Calculation of the numerical sample slope average from this histogram and comparison with the reference standard demonstrates that the sort has stabilized.

DETAILED DESCRIPTION OF THE INVENTION

Figure 1A:
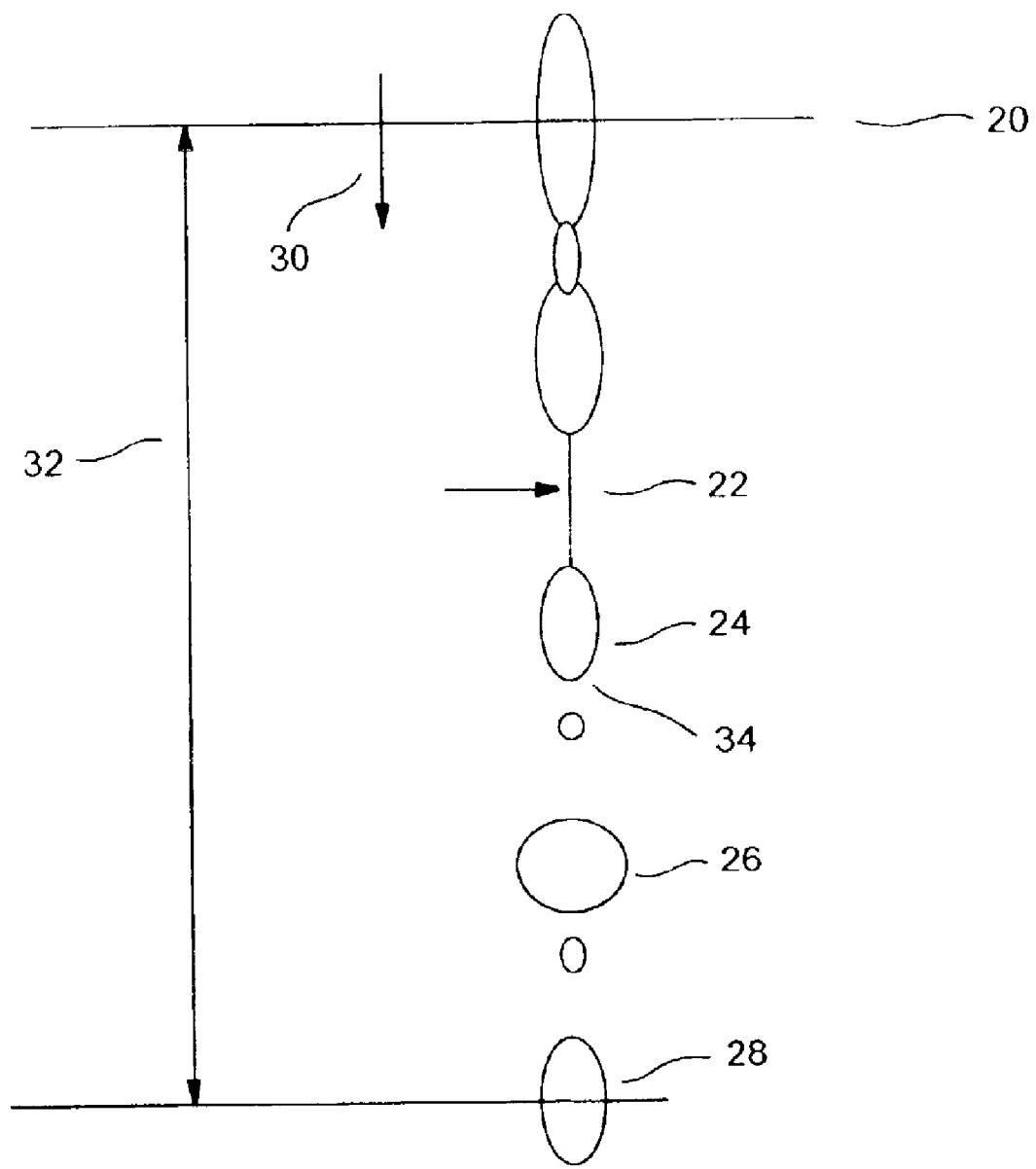
FIG. 1A is a schematic illustration of a droplet forming region of a particle sorter, demonstrating the proximal point at which the stream exits the nozzle 20, the neck of the jet 22, the last attached drop 24, the first free drop forming a sphere 26, the second free drop forming an ellipse 28, the direction of fluid flow 30, the area of multiple wavelength periods 32 and the distal point at which droplets break off from the jet 34.

The present invention provides systems for sorting particles in a suspension or fluid sample, methods of sorting particles in suspension or fluid sample, and sorting flow cytometers or apparatus for sorting particles in a suspension or fluid sample. These systems, methods and apparatus overcome several deficiencies of the art, and are most particularly directed at achieving a stable sorting system.

While trying to optimize the flow of a particle-containing suspension in a sheath through a conventional flow cytometer, a number of parameters that affect the sort of particles, including the viscosity of the jet, vary. Specifically, since changes to the viscosity have been found to be due to temperature change, which is not normally controlled by the instrument, the inventors compensated for viscosity and other variations by varying a number of parameters that affect droplet formation including frequency of the droplet generator, amplitude of the frequency of the droplet generator and pressures, including the sample and sheath pressures, among others, and thereby offset the change in viscosity.

It was further found that the range of frequencies that gave a stable droplet breakoff point was narrower than the range of pressures that would accomplish a stable droplet breakoff. One complication of adjusting sheath pressure to compensate for the variation in viscosity was that the pressure of the sample suspension had to be increased or decreased by a similar amount. If the pressure of the sample was not properly adjusted, the flow of the sample would accelerate or decelerate, which disrupted the ratio of particles (cells)-to-droplets required for high sorting yield.

As described in detail below, the present invention compensates for these and other problems of the art by providing at least one numerical reference standard generated from multiple images of a selected portion of the jetting stream, preferably the droplet forming region, when the sort is operating at a desired efficiency and stability. Thereafter, during the sort, multiple consecutive running images of the same portion of the stream are continually used to generate sample average numerical values that correspond to the reference standard. The sample average values are continually compared to the reference standard and any significant deviation found in a sample average from the reference standard triggers an adjustment of a sorting parameter to correct the sort and bring the subsequent sample averages back into substantial identity with the reference standard. This system thus continually corrects itself to stabilize the sort. As an example, one such adjustment involves utilizing electronic pressure regulators, enabling the sheath and sample pressures to be adjusted electronically, thereby allowing computer control of the sorting parameters.

The detection of deviations and resulting adjustments may be performed automatically through use of a computer program directing the method of this invention, thereby eliminating the time-consumption and cost of manually maintaining the stable sort operation.

I. Definitions

By the term "suspension" or "sample" as used herein and throughout the specification is meant to describe any liquid or solution that can be analyzed according to the invention. The sample can be anything that differs from the sheath fluid and is passable through the tubing of the flow cytometer to the flow cell. Typically, the suspension contains one or more particles that can be analyzed according to the present invention. The particles can be dispersed in the suspension. Such suspensions can optionally include, without limitation, agents such as detergents, sphering agents, dyes, including fluorescent dye molecules that bind specifically to the constituents to be measured, buffers, including those described in U.S. Pat. No. 3,962,125, preservatives, potentiators, antimicrobials, diluents, acids and bases, among others. Preferably, the suspension contains fluorescent dye molecules that are bound and unbound to the particles contained therein.

By the term "particle" as used herein and throughout the specification is meant to describe any object that can be analyzed according to the present invention. As used herein, the term particle includes, without limitation, viruses, bacteria, plant and animal cells that are obtained from whole blood or tissue samples or from a blood component such as plasma or serum. Preferably, the term particle includes, without limitation, white blood cells, red blood cells, peripheral blood lymphocytes, and cells derived from tissue and biopsy samples.

The term "sheath" or "sheath fluid" as used herein and throughout the specification is meant to describe the physical medium into which the suspension or sample is dispersed to accomplish sorting. The sheath fluid is generally an inert, electrically conductive, liquid into which the sample is dispersed. A number of sheaths are used in the art and include, without limitation, water and salt solutions, including saline. Preferably, the sheath is isotonic saline (Beckman Coulter, Inc., Miami, Fla.). Ideally, the sheath is invisible at the sample analysis point. It is conductive to allow the charge to get to the last attached stream segment, (previously known as the last attached drop). Sheath pressure is a major factor in the velocity of the jet.

By the term "stream" as used herein and throughout the specification is meant to describe the physical medium that contains the sheath medium and a suspension of particles that flow through the apparatus of the invention. More specifically, the stream comprises the sheath and the particles combined. The stream includes the portions prior to exiting the nozzle, after exiting the nozzle and after droplets are formed.

By the term "jet stream" or "jet" as used herein and throughout the specification is meant to describe the portion of the stream that has exited the flow cell exit nozzle or droplet generator of the flow cytometer. More specifically, the jet comprises undulations or curves, having peaks and valleys between the peaks. The valleys are also referred to as "neck" regions. The jet also includes the free droplets, which form downstream, in the manner of water exiting a hose. The velocity of the jet is a major factor in the rate that the sample moves from the analysis point to the last attached stream segment. In a flow cytometer, the jet is exited with a piezo oscillator to create a precise point at which the jet goes from connected undulations into free drops, forcing a known break off point.

By the term "droplet" as used herein and throughout the specification is meant to describe discretely formed sections of liquid sample of the jet that have separated from the continuous jet, generally after a neck region, leaving the exit nozzle. The droplets formed using the present invention can have a number of different shapes. Typically, the droplets are spherical or elliptical in shape.

By the term "breakoff point" as used herein and throughout the specification is meant to describe the location in a stream where a droplet fully separates from the continuous jet leaving the exit nozzle.

By the term "imaging means" as used herein and throughout the specification is meant to describe any device that can capture or generate the image of a stream sample according to the present invention. The imaging means obtains images of the jetting stream with a known phase relationship to the droplet generator. Components of the imaging means include an illumination field and an image capturing means such as a camera.

By the term "net charge" as used herein and throughout the specification is meant to describe a positive, negative, or neutral charge.

By the term "maintenance of the stable sorting system" as used herein and throughout the specification is meant to describe the ability to keep the values relating to the established sorting system constant. The values are determined by the jet geometry. The ability to maintain the established sorting system includes the ability to monitor the values, and adjust and readjust processing parameters to correct for unwanted changes that occur to the jet during the sort.

The terms "crystal drive" and "crystal frequency" as used herein and throughout the specification are meant to describe the signal to the droplet generating device. Crystal drive refers to the amplitude of the signal and crystal frequency refers to the frequency of the signal. In a preferred embodiment of the present invention, a piezo device is excited with a varying voltage signal, the frequency of which determines the droplet generation rate and the amplitude of which affects the droplet break off point.

By the term "sample pressure" is meant the pressure within the flow cytometer that is used to drive the sample to the flow cell. This could be alternatively, a syringe drive. Sample pressure is controlled by an electronic pressure regulator, which is controlled by a processor in the flow cytometer. Sample pressure varies as sheath pressure varies to keep the relative volumes consistent in the flow cell and sort stream.

By the term "sheath pressure" is meant the pressure within the flow cytometer that is used to drive the sheath to the flow cell. This could be alternatively, a syringe drive. Sheath pressure is controlled by an electronic pressure regulator, which is controlled by a processor in the flow cytometer.

II. The Method and System of the Invention

The present invention provides systems, apparatus, and methods for sorting particles of a sample, for controlling droplet formation of a stream, and for maintaining a stable sorting system.

The systems, apparatus and methods for sorting particles of the present invention overcome the deficiencies of the art by capturing a group of multiple images of selected portions of a jet in an established stable sorting system and producing a numerical reference standard that represents a statistical average of the multiple images.

The inventors have discovered that by capturing and averaging multiple images of a stable, efficient sort, a numerical reference standard can be generated and used to maintain the stability of the sort. The analysis of multiple images minimizes the noise that is present in the individual images of the prior art. By capturing multiple images of the sorting process continually throughout the sorting process, and generating multiple running sample averages that correspond to the standard, one may compare the numerical sample averages to the reference standard and detect and correct any deviations therefrom.

This method has a number of advantages over the prior art's methods of comparing successive images of the sort or comparing outlines of the images. The inventors have determined that by comparing sample values that are "numerical averages" derived from multiple images, insignificant deviations in the sort process are averaged out, thereby preventing unnecessary sort parameter adjustment. However, the "average values" generated from multiple running images of the sample enable direct comparison during the sort to the "ideal" reference standard, thereby simplifying the maintenance of a more stable sort.

Thus, in one embodiment, a method for sorting particles in a stream of a sample in a flow cytometer comprises the following steps. First, multiple images are captured of a portion of the stream and background noise is subtracted therefrom in a stable sort having desirable sort characteristics. These multiple consecutive images of a desired stable sort are translated and averaged into a single reference standard. This reference standard represents an ideal stable sort for the specific sorting operation.

Thereafter, during the sorting operation, groups of multiple images, from which background noise is preferably subtracted, of the same portion of the stream are continuously collected. A desired multiple of such sample images is then translated and averaged to form a "sample" average value representing the sample sort at a desired interval. Preferably a group of multiple sample images used to derive the average value are consecutive running sample images. By the term "running" as applied to the images is meant a series of consecutive images. For example, if the first multiple of images used to generate a sample average value is image 1 through image 10, the next consecutive "running" sample average value is generated from images 2–11, then 3–12, and so on. Thus, each sample average value is preferably generated by analysis of subsequent groups of consecutive multiple running images of the sort stream.

According to this method, each sample average value is compared to the reference standard. Any significant deviation(s) of a sample average value from the reference standard provokes a signal to adjust one or more of the processing parameters of the sort in the cytometer as a function of the deviation. The necessary adjustment thus minimizes the deviation in subsequent sample average values obtained from the sort and maintains the stable sort of the reference standard.

This method of image-derived numerical averaging to obtain the numerical standard and average values may also be used in other embodiments or variations of this method, that further include one or more conventional flow cytometry steps, including, without limitation, serializing particles in a stream; generating droplets from the stream; charging the droplets of the stream; deflecting the charged droplets; and collecting the deflected droplets. For example, this image-derived numerical averaging technique may be applied to methods including one or more conventional flow cytometry steps, such as serializing particles in a stream having flow velocity; generating droplets from the stream that have a common initial trajectory, with each of the droplets being formed from a corresponding jetting stream segment; applying a time-varying electric field to the stream so that the droplets are charged as a function of characterization of the contents of the corresponding stream segments; deflecting the droplets so that the post-deflection trajectories of the droplets are a function of the charges; and collecting the droplets in groups having common post-deflection trajectories.

It is anticipated that any conventional particle sorting system may be adapted to include the image-derived numerical averaging methods described herein and described in further detail below. Specific examples of the numerical values and their derivation are detailed below in the description of imaging and deviation.

The present invention also provides systems for sorting particles in a stream. In one embodiment, systems for sorting particles in a stream are provided which include an imaging apparatus for producing multiple images of a portion of said stream from which background noise is optionally subtracted. An automated, e.g., computer-assisted, device generates from multiple images of a stable sort having desirable characteristics the averaged numerical reference standard representative of said stable sort. An automated, e.g., computer-assisted, apparatus continuously collects during the sorting process multiple running images of said portion of the stream from which background noise is optionally subtracted and generates from the multiple running images at least one numerical sample average that represents the sample sort of each collection of the multiple running images. An automated, e.g., computer-assisted, means is used for comparing each numerical sample average to the numerical reference standard and determining whether any of said sample averages exhibits a significant deviation from the reference standard. The system also includes a device or apparatus for adjusting a processing condition of the sort in said cytometer as a function of the deviation, if necessary. The adjustment is necessary to minimize the deviation in subsequent sample averages to maintain the stable sort of the reference standard.

A number of conventional particle sorting apparatus, including flow cytometers, may be adapted to perform this invention with little or no apparatus modifications. Conventional flow cytometers for sorting particles in a stream generally include a flow means, a droplet generator, a detection means, an adjusting means, a charging means, a deflection means and a collection means. Other apparatus for performing the method of this invention may include, more specifically, a flow means comprising a conduit having an exit nozzle for creating a jet; a droplet generator for generating droplets from the stream, the droplets having a common initial trajectory, each of the droplets being formed from a corresponding jetting stream segment; a detector for providing a characterization of the contents of the stream; a charging apparatus for applying a time-varying electric field to the stream so that the droplets are charged as a function of characterization of the contents of the corresponding stream segments; a deflector for deflecting the droplets so that the post-deflection trajectories of the droplets are a function of the charges; and a collector for collecting the droplets having common post-deflection trajectories.

Preferably, the useful flow cytometers include, without limitation, the COULTER® TPS (Beckman Coulter, Inc., Miami, Fla.), the COULTER® EPICS® IV (Beckman Coulter, Inc., Miami, Fla.), the COULTER® EPICS® V (Beckman Coulter, Inc., Miami, Fla.), the COULTER® EPICS® C (Beckman Coulter, Inc., Miami, Fla.), the COULTER® EPICS®750 SERIES (Beckman Coulter, Inc., Miami, Fla.), the COULTER® ELITE™ (Beckman Coulter, Inc., Miami, Fla.), and the COULTER® EPICS® ALTRA™ cytometer (Beckman Coulter, Inc., Miami, Fla.) as well as those described in Lindmo et al., "Flow Sorters for Biological Cells" in Flow Cytometry and Sorting, 2$^{nd}$ ed. Wiley-Liss, Inc.: New York, N.Y. (1990), pages 145–169 and U.S. Pat. Nos. 4,361,400; 4,981,580; 5,700,692; 5,602,039; and 5,483,469, among others. These classical flow cytometric sorters can be utilized in the present invention with certain modifications to accomplish the method of this invention and include the following components.

Figure 1B:
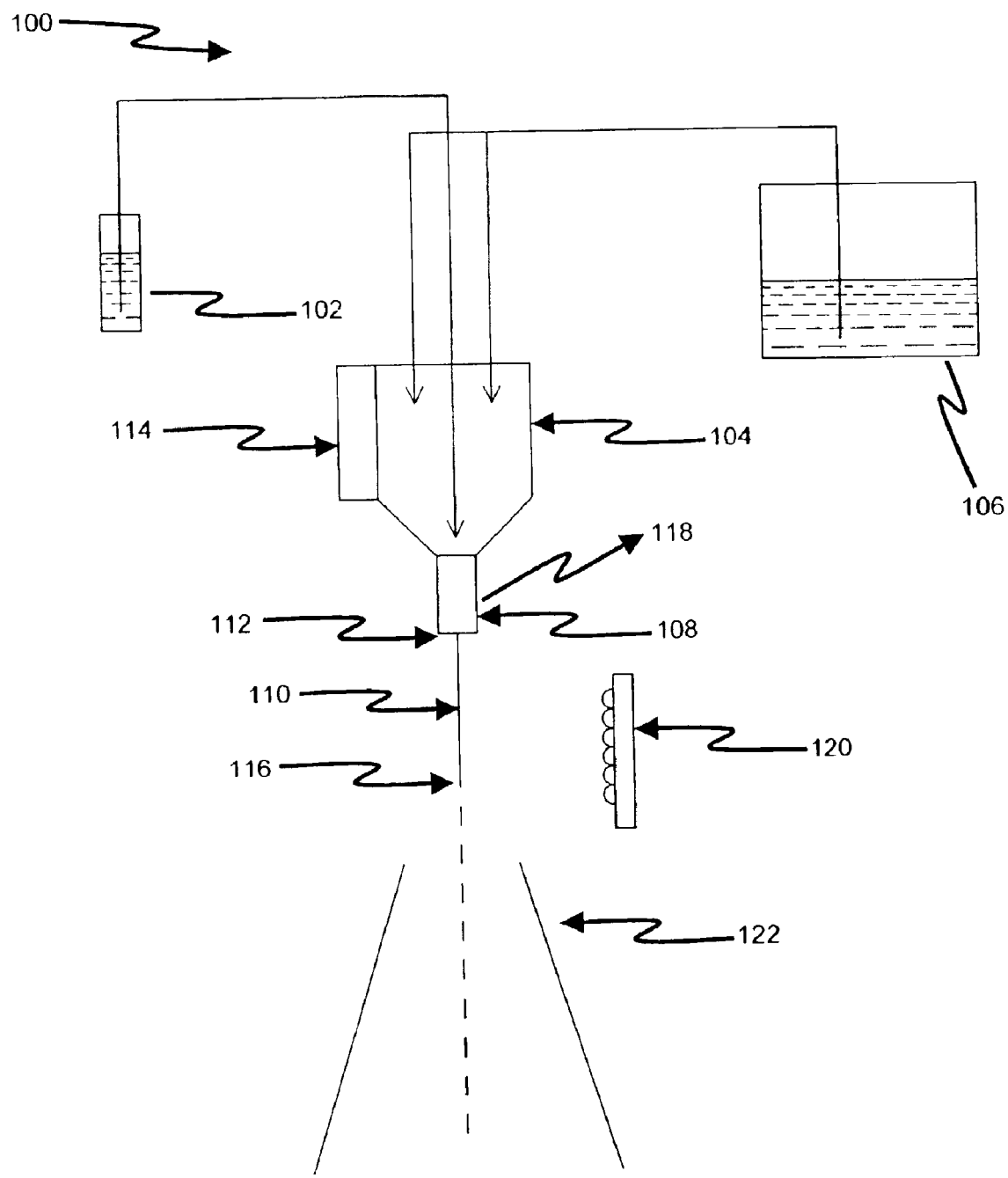
FIG. 1B is a flow diagram of a particle sorter process including a flow cytometer.

The following description of the particle sorting process refers generally to FIGS. 1A and 1B.

A. Flow Cell Chamber

One component of the system of the present invention, useful in the method of the present invention is a cell sorter 100 which provides for sorting of cells or particles in a suspension which are contained in a sample reservoir 102. The suspension is forced into a flow cell chamber 104 where sheathing fluid from a sheathing fluid reservoir 106 surrounds the sample as the sample enters the flow cell 104 from the sample tubing. This combination of sheath fluid and sample focuses the suspension into a serialized order in the resulting stream. The flow cell 104 provides an analysis point where the focused sample intersects a laser beam 108. The differences between the sample and sheath described above are detected in the flow cell 104.

The serialized suspension sheathing fluid mixture 110 exits the conduit of the flow cell chamber 104 through an exit nozzle 112. Preferably, a steady state flow of the stream 110 is established. Typically, pressures of about 0.5 to about 10 atmospheres (atm) are utilized in the present invention. However, one of skill in the art would readily be able to adjust the pressure.

B. Droplet Generator

A droplet generator 114 is also included as a further component of the present invention. The droplet generator 114 perturbs the jet. By doing so, waves of undulations travel down the jet at the velocity of the jet. Preferably, a piezoelectric crystal is utilized to accomplish perturbation of the jet. The frequency of perturbation is set by a frequency generator (not shown), and may be varied as determined by one of skill in the art. The drive amplitude is set by an amplifier (not shown). The jet forms as the stream is forced through the exit nozzle 112 and breaks into droplets at the droplet generator drive frequency.

The elapsed time between the time the sample is detected by the laser 108 in the flow cell 104 to the time that the stream is charged is called the delay time. The delay time must match the transit time of the desired sample from the analysis point to the last attached stream segment 116. The stream configuration must place the last attached stream segment 116 in the same position as the sample to ensure good sorting results. The stream configuration is manipulated in the present invention.

With regard to FIG. 1A, typically, the jet stream or jet includes the droplet forming region of stream 32. Specifically, the jet stream or jet includes the neck 22, the last attached drop 24, and the distal point 34 at which droplets break off from the contiguous jet. Preferably, the formed droplets have a common initial trajectory. A desired rate of droplet formation can be achieved by adjusting the crystal frequency while the sheath pressure and crystal drive will affect the position of the last attached drop.

C. Detectors

Another component useful in the present invention is a detection apparatus 118, which monitors the stream for specific particles and provides a characterization of the contents of the stream. Typically, the suspension and the sheath fluid stream 110 typically flow into a cuvette (not shown), which is illuminated by a light source 108. Preferably, the cuvette is present in a visualization chamber or portion of the flow cell 104. However, other chambers may be utilized to contain the suspension to be analyzed and may be selected by one of skill in the art. Suitable light sources include, without limitation, arc lamps, lasers, light bulbs, light emitting diodes (LED), among others. Typically, the light source 108 operates in a continuous mode.

While only one light source 108 and detector 118 may be employed for particle characterization, it is understood that multiple sources and detectors can be used for more complex characterizations and in more complex cytometers. In FIG. 1B, a light source (laser) 108 is focused on the stream above the nozzle 112. In an embodiment, in which a fluorescent (or other) dye is incorporated into the sample, this light source can excite the dye molecules, both bound and unbound. By doing so, the dye molecules fluoresce at a known wavelength. The intensities of scatter and fluorescence due to passing particles in the illumination area are detected by detectors. Still other light sources and detectors may be focused on the stream below the nozzle, and above the droplet forming region.

The detector outputs are digitized by an analog-to-digital converter (ADC) (not shown). The digital data is then analyzed by digital data processor (DDP) (not shown) to determine whether a particle is present and, if so, if it is of interest. Alternative methods of detection are also well understood by those of ordinary skill in the art.

D. Imaging Means

A further component of the present invention includes an imaging means 38 (See FIGS. 6 through 12) to capture an image of the jet below the nozzle 112 according to the present invention. The imaging means can be located in a variety of positions to capture one or more views of the jet, but is preferably located at the droplet forming region 32 (see FIG. 1A) in the performance of this invention. A variety of imaging means are known in the art and can be utilized in the present invention and include the imaging means described herein.

Some flow cytometers employ as the imaging means a wide width light field 120, e.g., LED screen, positioned behind the stream 110 and a video camera, e.g., a CCD camera positioned on the opposite side of the stream from the illumination. In one embodiment, the imaging means has one or more light fields or optical sources. Typically, the optical source 120 is capable of illuminating one or more portions of the stream. Preferably, the optical source 120 generates signals including wavelengths, which include, without limitation, those in the X-ray, UV, visible, and infrared region, among others. Preferably, the imaging means does not interfere with the signals received by the detectors from the illuminated particles.

When the optical source or light field 120 illuminates the jet 110 below the nozzle 112, it strobes light at a frequency that is the same as the frequency of the droplet generator 114, e.g., the piezo oscillator, of the flow cytometer 100. The light field 120 can strobe light at the same frequency as the oscillator. In one embodiment, the imaging means is operated at a frequency of about 0.6 to about 100 kilohertz; however the frequency may be adjusted by one of skill in the art as needed.

In illuminating the jet 110 below the nozzle 112, the light source 120, LED, illuminates the jet and appears to freeze the jet in a fixed position, as seen by the image capture device or detector, e.g. a camera, where in reality the undulations in the jet are actually traveling down the jet at a similar velocity of the jet stream.

In one embodiment, the image capture device includes a charge coupled device (CCD). In other embodiments, a video capture camera, a capture card, which converts a video image into a bitmap. Other analog devices known by those skilled in the art can be used. The camera collects the light from the LED 120, which is interrupted by the jet 110, if present, producing the image of the jet. The camera can view the jet from various positions along the length of the jet and is a moveable or fixed element in a flow cytometer. In such analog devices, the images are passed to the capture card for digitization. Alternatively, the imaging means can be a digital camera that produces a digital image without a capture card. The images are then passed to a processor (not shown).

Typically, the imaging means is utilized to obtain images of a selected portion of the jet 110. Thus, in the present invention, the camera is positioned within a flow cytometer to view the jet 110 from the exit nozzle 112 to the last attached stream segment 116. More specifically, the selected portion of the jet includes as the proximal point, the point of the stream or jet at which it exits the nozzle 112, and as the distal point, the point at which droplet breakoff point occurs, i.e., the point at which the contiguous stream or jet transitions into individual droplets. As described in FIG. 1A, the selected portions of the jet include the neck of stream 22 and the last attached drop 24. Preferably, the selected portion of the jet includes the last attached drop. Still other portions of the jet may be examined, such as the entire droplet forming region or the portion of the stream comprising the neck of the stream prior to the first drop that fully separates from the stream. However, other portions of the jet may be similarly analyzed.

In the performance of the method of this invention, as mentioned above, multiple images of the jet, or a preferred portion thereof, are typically obtained and averaged in the performance of the present invention to maintain a stable sort. The number of images obtained should be enough to avoid unwanted and unnecessary adjustments to the equipment, but not so many which would require acquiring the images over too long of a period of time. Typically, obtaining multiple images of less than about 3 images results in making unwanted and unnecessary adjustments to the equipment due to presence of large amount of unwanted noise. Similarly, obtaining more than about 40 images generally requires too much time and occupies more space on the computer than is warranted. In view thereof, preferably about 5 or more images of the jet are obtained. More preferably, about 5 to about 40 images of the jet are obtained. Even more preferably, about 5 to about 25 images of the jet are obtained. Most preferably, about 10 images of the jet are obtained. Typically, the multiple images are successively or consecutively obtained.

E. Means for Generating the Numerical Standard and Sample Averages

It should be understood in the following description that the apparatus and means for processing the images, for generating the numerical standard and sample averages, as well as for comparing the averages and generating the result can be encompassed in a single information processing device. This device may be a computer or employ computer programs. Selection of the appropriate processing device is within the skill of the art, given the teachings contained herein.

Typically, the image of the jet (see FIG. 2B) contains noise. Typically, the noise present in the images is generated by the optical illumination source or light field 120. However other components of the instrument can generate undesirable nose in the images. By reducing or eliminating the noise, a more accurate representation of the jet can be obtained. Thus, in order to obtain an accurate image of the jet to be analyzed, the residual noise present in the images of the jet should be eliminated or minimized. Typically, the noise is eliminated by subtracting a background image. The present invention therefore provides for obtaining one or more background images that contain noise (see FIG. 2A). The background images are typically obtained with no sheath or suspension fluid flow present. In order to obtain an accurate background image, multiple images of the background without sheath or suspension fluid flow are obtained. Preferably, about 5 or more background images are obtained. More preferably, about 5 to about 40 background images are obtained. Even more preferably, about 5 to about 10 background images are obtained. Most preferably, about 10 background images are obtained. The multiple background images can optionally be averaged to obtain a background image that is then used according to the invention.

Both the background images (FIG. 2A) and actual images (FIG. 2B) of the jet can then be enhanced using software and computer assisted media known to those of skill in the art. Typically, the images are enhanced using techniques including, without limitation, scaling, by dynamically increasing the image, image filtering and smoothing, among others. See, texts such as "Digital Image Processing", R. C. Gonzalez and R. E. Woods, eds., Addison Wesley Publishing Co., 1992 and "Pattern Recognition Principles", J. T. Tou and R. C. Gonzalez, eds., Addison-Wesley Publishing Co. 1974.

Once the background image and image of the jet are obtained and the same enhanced, the background image is subtracted from the image of the jet to remove noise. See FIG. 2C. If the background image and image of the jet are of the same size, no additional manipulations may be required prior to subtracting the background image from the image of the jet. Conventional and useful noise reduction techniques are also described in the text of Tou and Gonzalez, cited above. If necessary, the images of the jet, before and after background subtraction, can be stored for manual or computer-assisted comparisons at a later date. Alternatively and preferably, the images are instantly obtained and displayed on a monitor. An advantage of the present invention however includes optimizing storage on a computer or optimizing the time required to display on a monitor and instantly processing the images according to the following without storing the same for later use.

After background subtraction, the images of the selected portions of the jet are processed using devices, computers, or techniques known in the art for image enhancement, among other functions known to those of skill in the art. See FIGS. 2D and 2E. An additional method of enhancing the image also includes techniques including extracting stream edge conditions by counting the pixels from one edge to the first dark pixel, then by counting from the opposite edge on the same line to the first dark pixel see, FIG. 2F.

After generating the multiple images from the imaging means and enhancing these multiple images, the images are processed to generate from the multiple images an averaged numerical reference standard representative of a stable sort for that sample type. Similar techniques are used to generate running average sample values for comparison to the reference standard.

Figure 3:
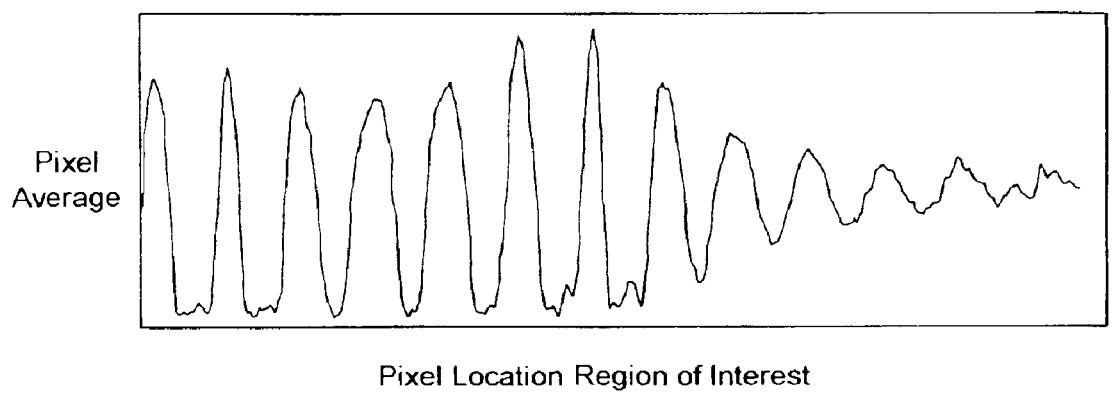
FIG. 3 is a histogram generated from the vertical integration of the pixel level of FIG. 2F.

In general, the processor of the flow cytometer takes a group of multiple successive images of an ideal or stable sort as described by the user of the method. Image processing and statistical analysis techniques known to those of skill in the art are employed to obtain a histogram for each image, or an average histogram based on multiple images for each group of multiple images. See FIG. 3. Preferably one-dimensional histograms of the images are generated by performing an integral operation along the Y-axis of the resultant image for each and every pixel along the X-axis of the resultant image. The desired multiple of images, e.g., 10, is used to provide ten histograms from which calculations are made. Alternatively, the multiple of histograms are averaged into a single averaged histogram from which a single value is derived. Each one-dimensional histogram or single averaged histogram is characterized by a downstream and upstream direction on the X axis, at least one neck region, and at least one undulation downstream of the neck region. The histograms generally contain multiple undulations having different sizes and correlating with each portion of the jet over time, including the necks, the last attached drop, the first and second free drops, satellites and the subsequent multiple wavelength periods. Each undulation of the histograms therefore includes a positive slope and a negative slope, a maximum value of peak height, peak width, distances between peaks, e.g., generally necks, and uniformity or inconsistency of peak sizes and shapes.

A number of software programs can be utilized to generate histograms from images and include the Scion Image program (Scion, Frederick, Md.) and MS Excel (Microsoft Corporation, California). Still other conventional statistics textbooks are available for instruction on creating a histogram. Noise that is not removed by background subtraction from the individual images may also be minimized by performing the histogram operation along the X-axis to establish upper and lower boundaries in the resultant image by scanning for some minimum pixel threshold before generating the histogram data along the X-axis as described below.

In one embodiment, therefore, a multiple of images from a stable sort are converted into individual histograms. From each histogram, a selected numerical value is calculated. The values from each histogram of the group of multiple histograms is then averaged to create the numerical reference standard. See FIG. 4A. An alternative method of generating the numerical reference standard is by converting the multiple images of the stable sort into a single average histogram and determining from the single average histogram a selected numerical average value that defines the numerical reference standard. The numerical averaged reference standard thus represents an ideal sort. Once the reference standard is established, the sample sort is run and groups of running multiples of images of the sample sort are collected, and individual or averaged sample histograms are generated as described above. At least one numerical sample average which corresponds to the reference standard is calculated which is comparable to the reference standard. Thus, in one embodiment, the multiple sample images are converted into individual sample histograms, and from each histogram a selected numerical value corresponding to the reference standard is determined. These numerical values from the multiple sample histograms of the multiple sample images are averaged to create at least one numerical sample average of the sample sort of each collection of multiple running images. Alternatively, the group of multiple sample images is converted into a single average sample and a selected numerical sample average value of the sample sort of each collection of multiple running images is generated from the average histogram.

The reference standard and the sample averages are generated from the histograms discussed above by the application of algorithms to the histograms.

As one embodiment, the reference standard average and/or the sample averages may be prepared from one or more of the following categories of numerical values generated from the histograms:

i. the slope of the upstream edge of an undulation appearing downstream of the neck region of each histogram;

ii. the slope of the downstream edge of the undulation appearing upstream of the neck region of each histogram;

iii. the average of the sum of the absolute values of the slope of the upstream edge of an undulation appearing downstream of the neck region of each histograms and the slope of the downstream edge of the undulation appearing upstream of the neck region of each histogram;

iv. the midpoint of the segment defining the slope of the downstream undulation of each histogram; and/or v. the integral of the area of the histogram between the lower of the slope values of slopes (i) and (ii).

The slope is calculated for numerical values of i., ii, or iii by using algorithms. Preferably, the slope is measured for an undulation of the neck of the droplet forming region. For example, the following positions are located on the histogram, each position having an X and a Y value: A is the peak of the histogram undulation corresponding to the last attached drop; B is the top of the last attached drop slope; C is the midpoint of the segment defined by B and D; D is the bottom of the last attached drop slope; E is the valley value of the last attached drop; F is the Valley value of the next upstream drop; G is the bottom of the next upstream drop slope; H is the midpoint of the segment between points G and I; I is the top of the next upstream drop slope and J is the peak value of the next upstream drop.

In an example, to generate the slope (i), the algorithms are: Slope=$((D_y-B_y)/(D_x-B_x))$ and $(I_y-G_y)/(I_x-G_x)$ where $B_y=A_y-20\%(A_y-E_y)$ and where it intersects the histogram provides $B_x$. $D_y=A_y-80\%(A_y-E_y)$, and where it intersects the histogram provides $D_x$. $G_y=J_y-80\%(J_y-F_y)$ and where it intersects the histogram provides $G_x$. $I_y=J_y-20\%(J_y-F_y)$ and where it intersects the histogram provides $I_x$. In addition, other positions on the segment of the line defining the slope can be utilized.

Where the reference standard is at least one of the slopes or combinations thereof, and in circumstances in which the sample average value of the slope deviates significantly from the standard, the processing condition to be changed is the crystal drive amplitude.

Another calculation can be used to establish the midpoint of the segment defining the slope of the downstream undulation of each histogram to provide a value that if it deviates from the corresponding reference standard, is indicative of the need for sheath pressure and sample pressure adjustment. The segment is the line between the two points B&D or G&I defining the slope. The midpoint of any indicated slope segment is obtained by adding the top and the bottom X&Y values and dividing those sums by 2. Cx midpoint=(Bx+Dx)/2, Cy midpoint=(By+Dy)/2.

Where the reference standard is the midpoint, and in circumstances in which the sample average value of the midpoint deviates significantly from the standard, the processing condition to be changed is the sheath pressure.

The integral value (v) of the histogram between midpoint C and midpoint H is the numerical value, which if it differs significantly from the reference standard, indicates catastrophic system failure.

According to this invention, once the reference standards of at least one of the values (i) through (v) above have been determined and stored for later use, corresponding sample average values from multiple running consecutive images are monitored during the sort.

Preferably, at least two algorithms are used to determine the deviations in the sort and correct the same. In another embodiment the algorithms employed in the present invention include, without limitation, the position, preferably the midpoint, of the line defined by the slope, the slope value and the integral of the area between the lower slope defining values, D to G. See, e.g., FIGS. 5A–5C.

Preferably, the algorithms applied to the histogram are applied to the region of the histogram corresponding to the last attached drop or to the downstream side of the neck, among others. A first algorithm determines the numerical value of the slope of the histogram curve to the downstream side of the neck. A second algorithm determines the position of the midpoint of the line segment defining the slope of the histogram curve which corresponds to the downstream side of the neck.

In one embodiment a reference slope value and position of the midpoint of the line segments defining the slope of the last attached drop of an optimal sort is first established. To determine reference values, the slope value and midpoint position of the slope of the curve of the histogram for last attached drop or neck region are thereby monitored until the same are stable for a given period of time, whereby successive images are captured, or until the user determines that the sort has been optimized. Once a stable position and average slope are noted, the average slope is calculated and the position of the midpoint of the average slope is determined. These reference values and positions are then stored and used as described below.

The generation of suitable algorithms, in addition to the algorithms identified herein, is well within the skill of the average person in this art. This method is not limited by the selection of any specific algorithm. Typically, computer-assisted media are utilized to apply analytical algorithms to the histograms as the means for determining the numerical values that can indicate deviation of the sort.

F. Deviation Means

The sample averages are then compared to the reference standard. If the sample averages varies less than a predetermined amount as determined by one of skill in the art as compared to the reference standard, adjustment of the flow cytometer or sort is not necessary. However, if the sample averages vary more than a predetermined amount as determined by one of skill in the art as compared to the reference standard, adjustment of the flow cytometer or sort may be necessary and is discussed below.

In order to correct the sort, to restore the initial sort conditions, or to optimize the appearance of the jet, a means for determining the deviation between the reference standard and sample average values generated as described above is required. Such deviations of these numerical values can be determined manually or by using automated or computer-assisted media. In one embodiment, the deviation between one or more sample values(s) and the reference standard is calculated from images measured from the point representing the proximal end of the droplet forming region where the jet exits the nozzle to a point representing the distal point at which the droplets break off from the stream.

In a preferred embodiment, once the indicated values are calculated according to this invention, the processor compares the sample averages, i.e., sample averages generated from multiple image collections to the reference standard to determine there exists a deviation in the sample averages from the numerical standard. A significant deviation is one in which some of the sort characteristics have changed to such an extent that adjustment of the sort parameters is necessary to stabilize the sort. The extent of a deviation sufficient to be significant would be determined by this invention. Thus, some deviations discovered during comparison can indicate that an adjustment of the sort parameters is necessary to 're-optimize' the sort. Alternatively, some deviations are so significant as to indicate a catastrophic failure of the cytometer and the need to stop the sort.

G. Adjusting Means

In order to maintain a stable sort, the system can be adjusted prior to and during sorting the particles of the suspension. If a significant deviation of sample average from reference standard is detected, the method involves an adjusting step, in which the processor is programmed to gives commands to the sample pressure regulator, the sheath pressure regulator and/or the piezo oscillator to force the deviant averages back to the reference standard representative of a sort in known, stable and desirable condition. If unable to do so, the processor then issues other commands to the sample pinch, sheath pinch, deflection voltage, stream charge and the user interface to stop the sorting and alerts the user.

By use of the multiple image averaging/numerical standard and sample value comparison process described above, stability of the sort can be maintained particularly throughout the sort. The operating parameters as described above can be varied and include the crystal drive, crystal frequency, pressure, including the sheath pressure, sample pressure, temperature, jet diameter, jet velocity, frequency, viscosity, and combinations thereof, among others. Preferably, the pressure, including the sheath pressure, and crystal drive are adjusted.

In one embodiment, if the comparison of the slope average reference standard with the sample slope average shows a variance in the sample of a significant amount, several parameters may be adjusted to return the slope value to the reference standard slope value. One of skill in the art would readily be able to determine the prescribed amount that the slope average may vary given the environmental conditions, sample being analyzed, and operator, among other factors. In one embodiment, if it is determined that the slope average has varied more than a prescribed amount, an adjustment to the flow cytometer may be made. For example, if a significant deviation occurred between the reference standard and sample average using the numerical values of (i), (ii) or (iii) above, the crystal drive may be adjusted. In another embodiment, if it is determined that the midpoint (iv) sample average has varied more than a prescribed amount, the sheath pressure and desirably, the sample pressure, without limitation, may be adjusted. Alternatively, if the midpoint value (iv) decreases as compared to the reference standard, the crystal frequency can be adjusted. The inventors have discovered that over time the midpoint of the slope of the corresponding curve of the histogram of the last attached drop may change. Typically, the midpoint of the slope of the curve corresponding to the last attached drop can increase indicating a lengthening of the jet, or can decrease, indicating a shortening of the jet. By observing the midpoint value of the slope of the last attached drop, parameters can be adjusted to restore the position of the midpoint of the slope to the reference value. Preferably, the midpoint value of the slope is compared with the midpoint slope of the reference standard. If the sample average varies more than a prescribed amount, parameters are adjusted to restore the midpoint of the slope to the reference standard. One of skill in the art would readily be able to determine the prescribed amount of variation in these numbers. Preferably, the sheath pressure is adjusted. In one embodiment, the sheath pressure is adjusted thereby returning the sample average midpoint of the slope value corresponding to the last attached upstream drop to that of the reference standard.

By use of this system and method of this invention, any loss of stability of the sort is detected, signaling the cytometer or operator to compensate for the encountered problems. Typically, the multiple image averaging/histogram comparison system of this invention is sensitive to any problem that affects the sorting of the suspension including, without limitation, catastrophic events such as trapped bubbles and clogged or plugged orifices, or instrument failure, i.e., any problem so severe as to require the stream to be stopped. In one embodiment, the system sheath flow, sample flow and deflection voltage can be shut off by automated or computer-assisted media. In another embodiment, the system is shut off manually where the system notifies the operator that a problem has been encountered, such as by a significant deviation in the value (v) above. Preferably, the operator is notified by use an alarm, message, or combination thereof. Such signaling modifications of flow cytometers are now conventional. Most preferably, the operator is notified by use of an alarm.

When computer assisted media are utilized in the present invention, one or more computer programs are typically utilized. A computer program is provided that performs the analysis and calculations described above and further generates the histograms described above. More specifically, the computer programs can be designed to record, sort and calculate the parameters of the system provided above and to obtain the necessary analytical results. Controlling the appropriate parameter is important. Standard equations governing droplet generation are known which can be used in the present invention. See the references cited above.

In a preferred embodiment, this computer program is integrated into or is in communication with the particle analysis instrument, particularly a hematology instrument or flow cytometer. In another preferred embodiment, the program is on a separate computer, which is a "plug-in" device for attachment to the analysis instrument. Still a further preferred embodiment of this invention is a computer program that is present on a standalone computer, into which data from the instrument is fed. Yet another preferred embodiment, the method of this invention can be generated by use of conventional spreadsheet programs on standalone personal computers.

This computer program includes means for comparing the sample average values generated by the multiple sample images of the stream to the reference standard of the stream having acceptable sorting parameters. This program also comprises a means for applying suitable algorithms to generate the numerical values from these histograms. Thus, the program preferably performs all of the calculations necessary to perform the method of this invention by analyzing the images. Preferably, the program sends a signal to the pressure regulator to control the sheath or sample pressure, to the droplet generator to control the droplet breakoff point or droplet frequency, to the sheath flow valve to stop the sheath flow, to the sample flow valve to stop the sample flow, and to the deflection plates to stop the deflection, among others. In still another embodiment of this program, the computer can provide a signal or warning for the operator when an aberrant result is identified.

H. Charging Means, Deflection Means and Collection Means

As mentioned above, the remaining functions of a sorting process or apparatus useful in the full performance of this system are conventional. For example, a charging means (not shown) is further utilized to establish a net charge of the droplets contained in the stream. Typically, the charging means applies a time-varying electric potential to the stream in phase with droplet formation at the appropriate time. One of skill in the art would readily be able to adjust the electrical charge required to appropriately charge the droplets in the stream. The charged droplets can then follow a common initial trajectory through two or more oppositely charged deflection plates 122. Preferably, the droplets follow a trajectory through a pair of oppositely charged electrostatic deflection plates 122. An electric field established between these electrostatic plates 122 will deflect the charged droplets such that the trajectories of the charged droplets are changed and are a function of the droplet charge values and the intensity of the electrostatic filed created by the charged deflection plates 122. Desirably, one plate has an about −6 kilovolt (kV) voltage applied to it, while the other plate has an about +6 kV voltage applied to it; this establishes an about 12 kV potential difference between the plates 122 which are spaced progressively farther apart.

A collector (not shown) is also provided which contains multiple compartments, where one compartment receives undeflected droplets, while the other compartments receive deflected charged droplets. The charge (or lack of charge) on a droplet is determined by an electric potential applied to the stream at the time the droplet breaks off from the stream.

A majority of conventional electrostatic sorting flow cytometers can benefit from the invention described herein.

III. Alternative Imaging Assembly

In a further and optional embodiment of this invention, an assembly for obtaining images of a fluid stream, for instance, within a flow cytometer or other particle sorting apparatus useful for performing the method and system of this invention, has a unique arrangement. The assembly overcomes certain deficiencies of conventional imaging assemblies of particle sorting systems of the prior art by dramatically improving image contrast. More specifically, image contrast is dramatically improved using a novel background illumination technique and/or apparatus of the present invention, thereby providing for more control in the sort. The improved image contains additional detail that allows a more accurate control of a particle sorter. Further, additional stream features such as satellite droplet formation can be observed, analyzed, and controlled as well. The following discussion is best illustrated in FIGS. 6–12.

A typical jetting stream is provided as a substantially clear liquid having a stream width of only about 50 to 100 microns. Prior art assemblies, such as assembly 200 illustrated in FIG. 6, typically utilize a light field, or illumination field, 202 that is approximately 60 to 120 times the width of the stream 204 to backlight the stream 204 relative to an aligned image capturing device 206 that is diametrically opposed to the illumination field 202 relative to the stream 204. The image capturing device 206 is typically any type of camera. The illumination field 202 is typically provided by a set of light emitting diodes 208, or any other strobable light source and a diffusion plate 210 that uniformly diffuses the rays emitted by the diodes 208.

The inventors of the present invention recognize that the stream itself functions as an optical lens. Thus, from the viewpoint of the image capturing device 206, at least a part of the illumination field 202 is imaged within the stream itself. For example, see lines 212 in FIG. 6 that illustrate the field of view imaged within the stream 204, and see the image 214 that appears within the stream 204 as seen by the camera 206. In addition, see lines 216 in FIG. 6 that illustrate the field of view defined by the angle of light acceptance of the camera 206. The field of view of the camera includes the stream 204 with a background image 214 therein and light emitted from the illumination field 202 passing adjacent and externally of the stream 204. Thus, the background image 214 imaged within the stream 204 is the same as the image of the illumination field 202 that appears on either side of the stream 204.

Figure 7:
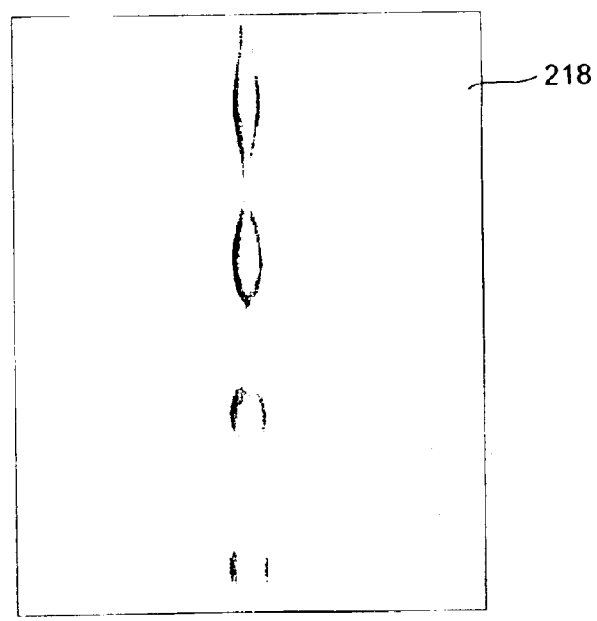
FIG. 7 is an image of the jetting stream produced by the prior art assembly of FIG. 6.

FIG. 7 is an example of an image 218 of the stream 204 taken by camera 206. Diffraction bends the light around the cylindrical stream 204 and creates a faint shadow that is visible to the camera. Thus, the image 218 of the jet stream 204 was obtained due to diffraction, which causes faint shadows around the perimeter of the jet stream. Further, since light reflects off the surface of the clear fluid droplets, faint images of the surface of the jet stream may be obtained; however, the edges of the stream that contain the important positional information cannot reflect light back to the camera.

Thus a novel imaging assembly useful in particle sorters and flow cytometers in general is provided, as well as an additional embodiment to the method and systems described above. According to this aspect of the invention, a novel imaging assembly 220 best illustrated in FIGS. 8 and 10 has a novel illumination field 222 and an imaging capture device 224. The stream 226 is located between the illumination field 222 and the imaging capturing device, or camera, 224, and the camera 224 is moveable laterally or horizontally with respect to the stream 226 so that an image of the appropriate portion of the stream 226 can be obtained. The field of view, or angle of light acceptance, of the camera 224 is sufficiently large to include greater than the entire width of the stream 226 as illustrated by lines 228 in FIG. 8. Zoom lenses may also be used to capture the appropriate portions of the stream and illumination field.

An opaque mask 230 is located between the illumination field 222 and the stream 226. The illumination field can be provided, for instance, as a set of light emitting diodes 232 covered by a light diffusing plate 234, and the opaque mask 230 can have openings therein so that the image 236 of the background within the stream includes both dark and light areas. Preferably, the openings form readily recognizable geometric patterns that appear within the jetting stream from the viewpoint of the image capturing device 224.

Figure 8:
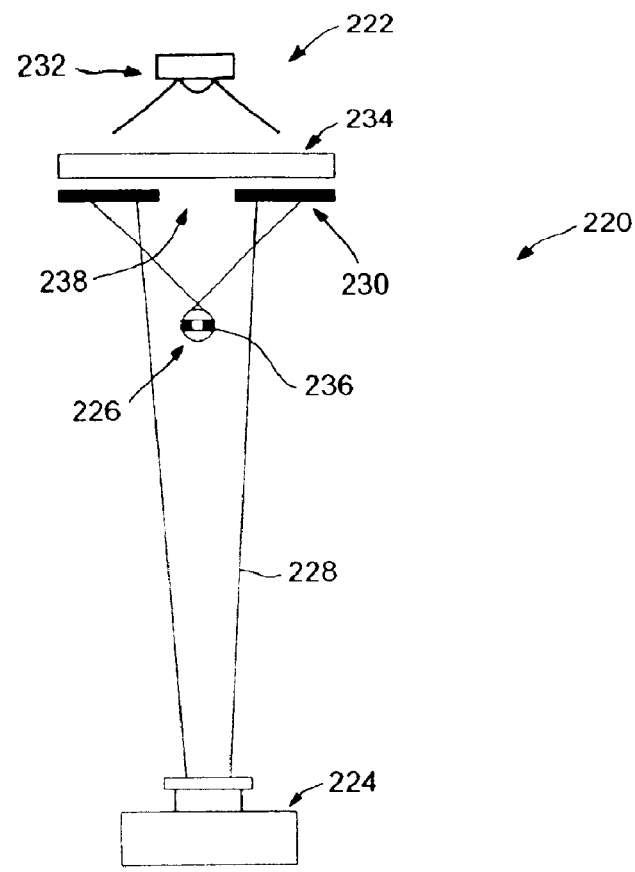
FIG. 8 is a plan view of an assembly for obtaining images of a jetting stream according to the present invention.
Figure 10:
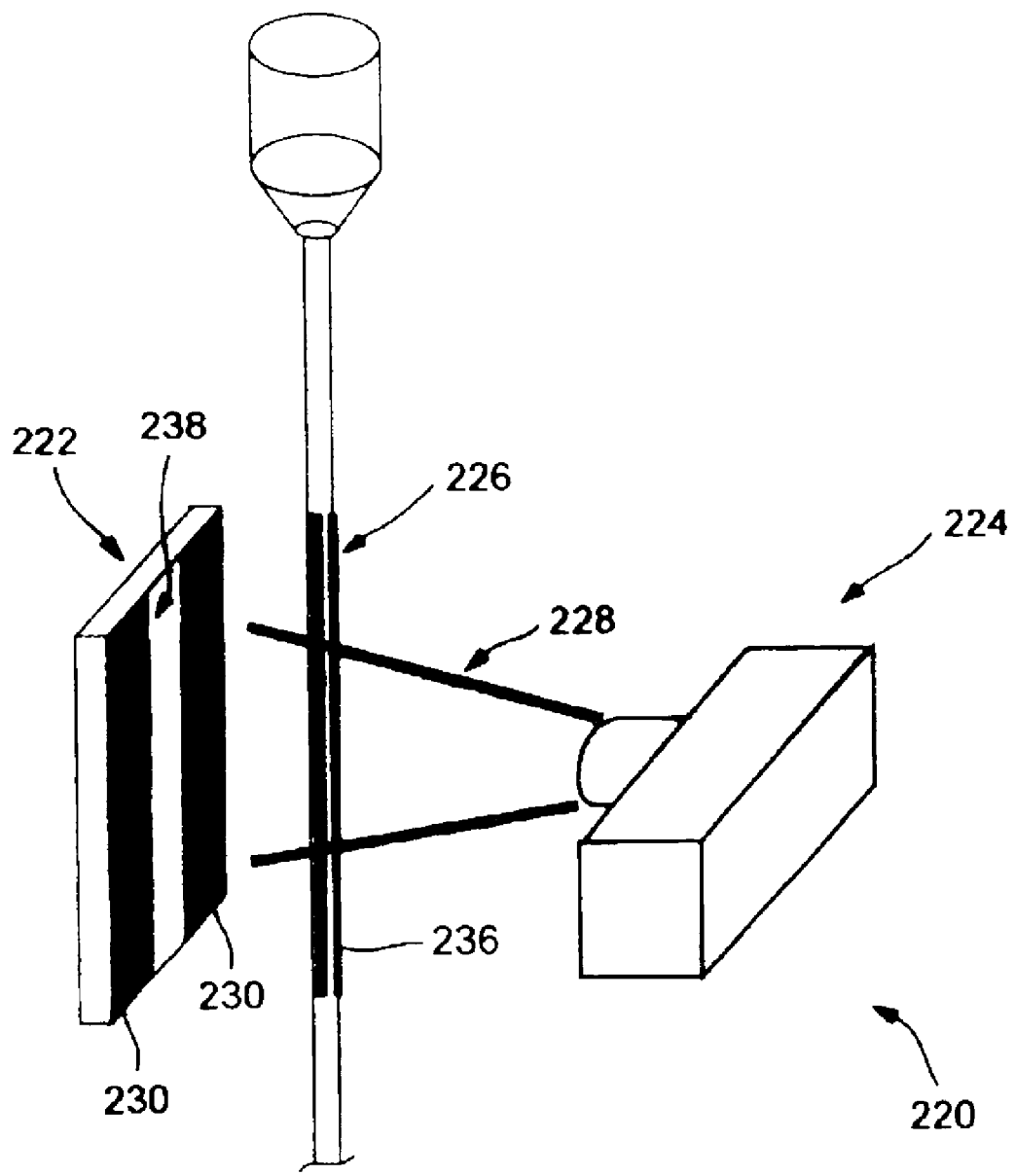
FIG. 10 is a perspective view of an assembly for obtaining images of a jetting stream according to the present invention.

As best illustrated in FIGS. 8 and 10, the dark areas provided by mask 230 preferably are imaged within the stream 226 along the outer edges of the stream 226 as viewed by the camera 224. For example, the mask 230 can be provided with a central elongate slit 238 that extends substantially parallel to the stream 226. Preferably, the width of the slit is about 3 to 30 times the width of the stream 226 so that the camera 224 captures the light that passes through the slit 238 and adjacent the outer edges of the stream 226 to provide dramatic contrast between the stream and background.

Figure 9:
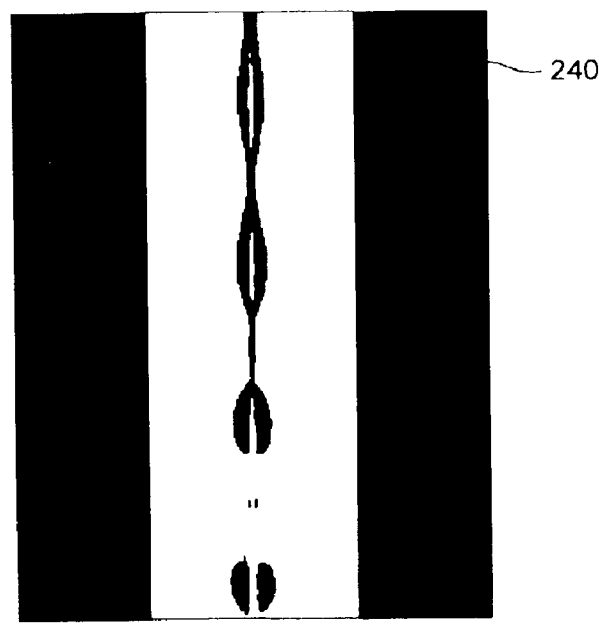
FIG. 9 is an image of the jetting stream produced by the assembly of FIG. 8 according to the present invention.

FIG. 9 provides an example of an image 240 taken by camera 224 according to the present invention. The stream 226, particularly the outer edges of the stream 226, is greatly contrasted by many orders of magnitude relative to the lighted background provided via slit 238. Thus, the actual shape of the stream 226 can be accurately determined from image 240. As discussed above, the image 240 is provided since the jet stream 226 functions as a cylindrical lens and images the dark and light areas of the background therein. To this end, the background image is reduced and reversed within the steam as viewed by the camera 224. Thus, the camera 224 captures the background image 236 within the stream 226 and captures the stream 226 against a lit background to produce a desired dramatic increase in contrast. A more detailed image of the jet stream is thereby produced.

Figure 11:
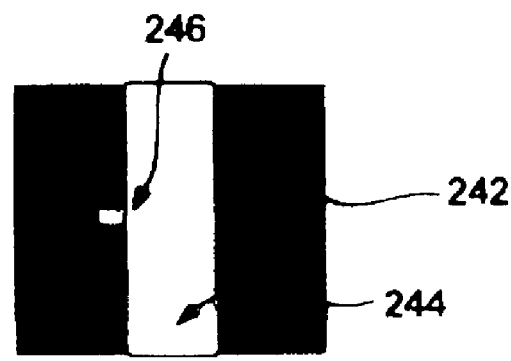
FIG. 11 is a front elevation view of an alternate embodiment of an illumination field according to the present invention.
Figure 12:
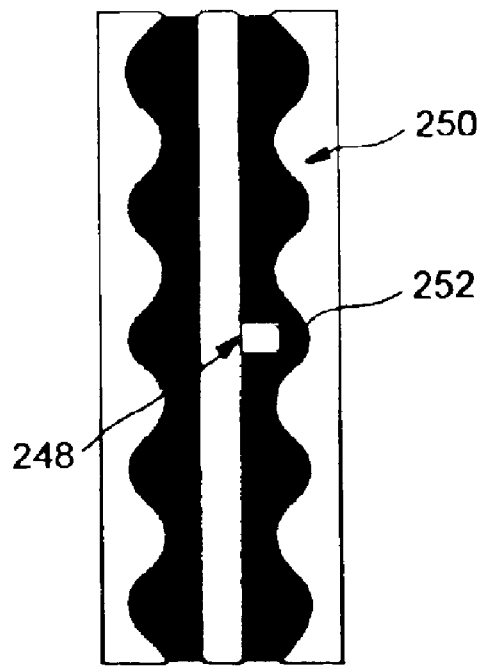
FIG. 12 is an image of an excited jetting stream illuminated by the illumination field of FIG. 11.

The mask can also be utilized to provide positional information. For example, a geometric pattern of light bordered by the mask can be imaged within the stream to provide distinguishing marks, for example, at predetermined lengths from an outlet nozzle through which the stream flows. To this end, FIG. 11 illustrates a part of a mask 242 that has an elongate central slit 244, as discussed above, and a relatively small rectangular opening 246 at a predetermined length along the slit 244. Thus, when a stream is illuminated using the mask, a distinguishing mark, tick or bar, 248 will be imaged within the stream corresponding to opening 246 in mask 242. This is best illustrated by image 250 of a stream 252 in which the distinguishing mark 248 is imaged. By use of such distinguishing marks, the undulations of an excited stream can be more readily detected and measured. In addition, the marks can be used to highlight the preferred break-off position or a relative distance position.

It is readily apparent that the imaging assembly according to the present invention may be employed in flow cytometry systems other than the multiple image averaging/histogram comparison method of this invention. Similarly, modifications may be made to conventional flow cytometers or new flow cytometers may be designed to contain the imaging assembly according to the present invention. The inclusion of the imaging assembly into a flow cytometer apparatus is thus considered to be a part of this invention, because the design of other components of a flow cytometer are well known in the art.

IV. EXAMPLES

The following examples are provided to illustrate the invention and do not limit the scope thereof. One skilled in the art will appreciate that although specific conditions are outlined in the following examples, minor modifications can be made which are equivalent to those specifically exemplified and thus are encompassed by the spirit and scope of the invention.

Example 1

Performance of the Method: Multiple Imaging/ Generation of Numerical Averages from Histograms This example demonstrates how the method and system of this invention enables the cytometer operator to maintain the stability of the sort in the event of a change in condition, e.g., a temperature change. According to this invention, the operator obtains images of the stream, specifically a selected region of the stream, generates a histogram display thereof, analyzes the histogram data to generate the reference standard and sample average values, and makes corrections for the change in temperature to stabilize the sort.

An isotonic sheath fluid with no sample particles was introduced into a commercial flow sorter, e.g., the COULTER® ELITE™ flow cytometer or the COULTER® EPICS® ALTRA™ flow cytometer (Beckman Coulter, Inc, Miami, Fla.). As imaging means, these cytometers contain an integrated CCD video camera, a commercial video digitizing processor (Integral Technologies, Indianapolis, Ind.), and a sort control software (Beckman Coulter, Inc., Miami, Fla.). These instruments have conventional illumination fields.

Figure 2A:
FIGS. 2A–2F show charge coupled device (CCD) images of the droplet forming portions of the stream. Specifically.
Figure 2B:
Figure 2C:
Figure 2D:
Figure 2E:
Figure 2F:

Multiple CCD images of the droplet forming region of the resulting stream were generated and the background image subtracted from the sample image. Specifically, FIG. 2A is an image captured with no sheath fluid flow. FIG. 2B is an image with sheath flow. FIG. 2C shows the resultant image after taking the absolute value of a pixel by pixel subtraction of the images in FIG. 2A and FIG. 2B. The image is then enhanced, resulting in the enhanced image of FIG. 2D. Further enhancement of FIG. 2D is accomplished by reducing the image by cropping extraneous portions of the stream to minimize the field of view, thereby increasing the resolution, resulting in FIG. 2E. FIG. 2F shows the image of FIG. 2E with the empty spaces in the jet filled in to allow generation of a desired histogram. The image of FIG. 2E is then used to perform an integral operation along the vertical direction for each and every pixel along the X-axis, generating a one-dimensional histogram (FIG. 3) for the entire stream.

Ten (10) successive images were similarly processed and the slopes and midpoints of the slopes calculated for this region of the stream were averaged to create reference slope and reference slope midpoint values. The program determined that this slope and the slope mid-point positions and 10 successive such positions were stable and indicated to the user that the system was stable. The operator then instructed the program to automatically control the sort stream, at which time the reference value of the slope and slope mid-point were established for a known stable system.

Figure 4A:
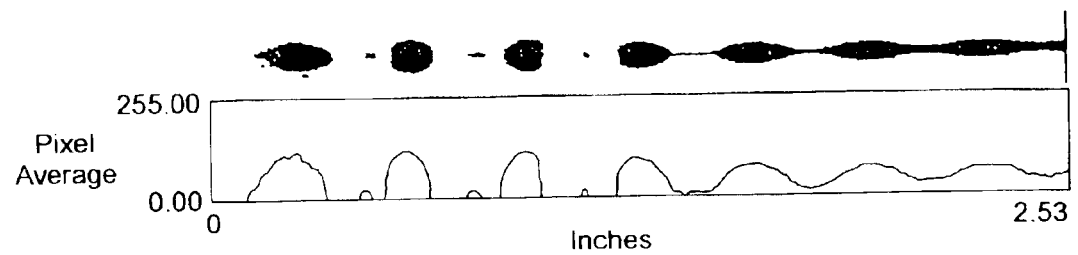
FIGS. 4A–4C are histograms generated from another flow that show the resultant images of the jet after background subtraction, enhancement, resolution optimization, the filling in of empty spaces, and corresponding histograms of the same.

FIG. 4A shows the resultant image of the jet after background subtraction, enhancement, resolution optimization, filling in of empty spaces, with the corresponding averaged histogram appearing below the images. This histogram permits determination of the neck, the last attached drop, the first and second free drops, satellites and the subsequent multiple wavelength periods. The height of each of the resultant histogram channels in FIG. 4A is the total number of pixels comprising the stream in the image of FIG. 2F. Each maxima and minima of the histogram was located and identified. Thus, the histogram of FIG. 4A is based on an average of 10 images of the same region of the stream. The numerical average reference standards for the slope and for the midpoint were calculated from this histogram and were 0.900 and 380.0, respectively.

Figure 4B:
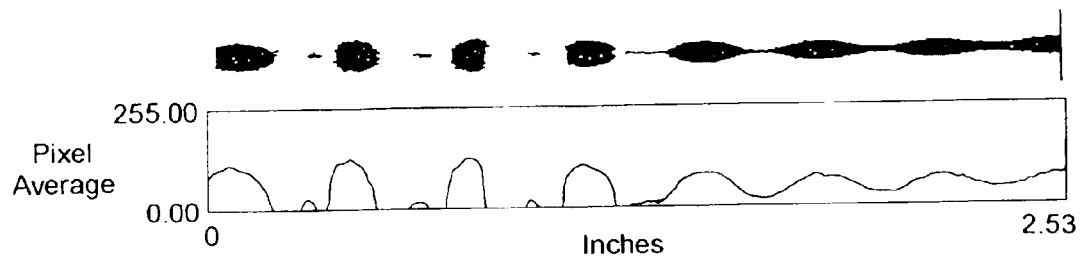

The temperature of the flow cytometer was then increased by about 5° C. The average of 10 successive sample images obtained is depicted in FIG. 4B and an average sample histogram generated therefrom. Algorithms were applied to the histogram to generate the sample average, i.e., the midpoint of the segment slope of a peak of the average histogram, corresponding to the reference standard. The numerical sample midpoint average in this instance is 387.6.

When comparing the sample average generated from the histogram of FIG. 4B to the reference standard generated from the histogram of FIG. 4A, the operator could observe a deviation in these numerical values of 7.6. This deviation means the sort stream changed after the temperature increase. The stream had lengthened and the droplets traveled further away from the nozzle. This deviation requires an adjustment of a parameter of the sorting system.

The sort control program of the present invention is constantly processing the images to generate numerical values of sample average slopes and sample average slope mid-point values which are compared to the reference slope and slope mid-point standards to determine if a change to the instruments parameters are necessary. The direction and amplitude of change is then computed and the instrument is instructed to make the change to the required parameter. In this case, a determination was made that a decrease in the crystal drive and a decrease in the sheath pressure was necessary. The crystal drive was decreased about 1% and the sheath pressure was decreased about 0.1 pounds per square inch (psi).

Figure 4C:
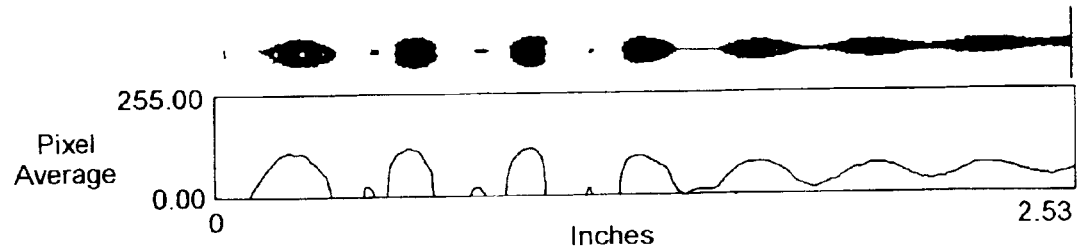

Generation of another histogram from multiple images of the jet following the pressure decrease and crystal drive decrease is shown in FIG. 4C. The sample average value calculated from applying the algorithms to this histogram was for the slope 0.900 and for the midpoint 380.0, i.e., substantially identical to the reference standards. Thus, the parameter adjustment enabled the operator to restore the stable sort indicated by the reference standard.

Example 2

Energy Coupling Variation

This example demonstrates the effectiveness of the present invention to obtain images of a stream, specifically a selected region of the stream, to analyze this region of the stream, and to make corrections in the sort where the change in sort conditions is caused by a change in energy coupling efficiency. Energy coupling efficiency can dampen the growth of the disturbance causing breakoff and correspondingly, affects the breakoff point. Energy coupling efficiency is the amount of energy transferred from the oscillator to the stream.

The method and system of this invention is performed as initially described in Example 1, except that after the reference histogram for a stable sort was established (FIG. 5A), the reference standards were calculated as 0.900 for the slope and 380 for the midpoint. A change in sort conditions resulted in a multiple (10) running consecutive sample histogram of FIG. 5B. The corresponding sample average was obtained by applying the appropriate algorithm to the histogram data of the direction and amplitude of the change of the slope was then computed by a suitable algorithm. By comparing the sample average value, i.e., the value of the positive slope of the first peak downstream of the neck generated from the data of histogram FIG. 5B to the reference standard, a deviation in the sample slope average was detected, i.e., the slope value decreased by 0.18. The sort control program of the present invention is constantly processing the images to create resultant sample slope averages and sample slope segment mid point values which are compared to the reference slope standard and slope segment mid point standard to determine if a change to the instrument parameters is necessary. If so, the instrument is instructed to make the change to the required parameter.

Figure 5A:
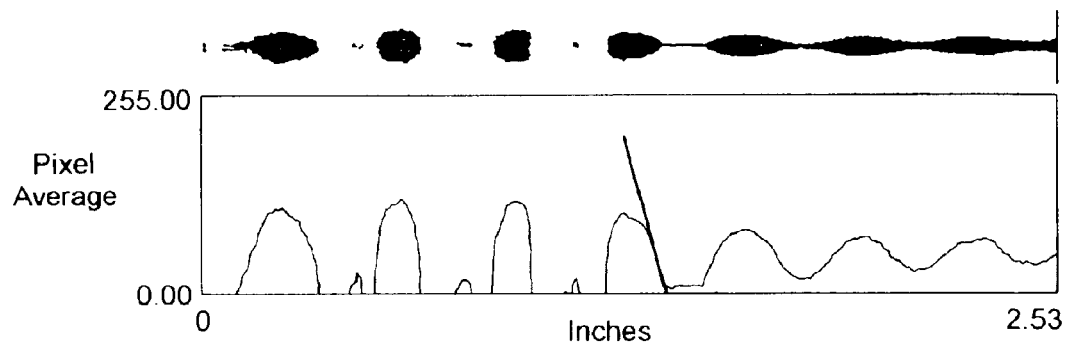
FIGS. 5A–5C show the resultant images of the jet after background subtraction, enhancement, resolution optimization, filling in of empty spaces, and corresponding histograms of the same.
Figure 5B:
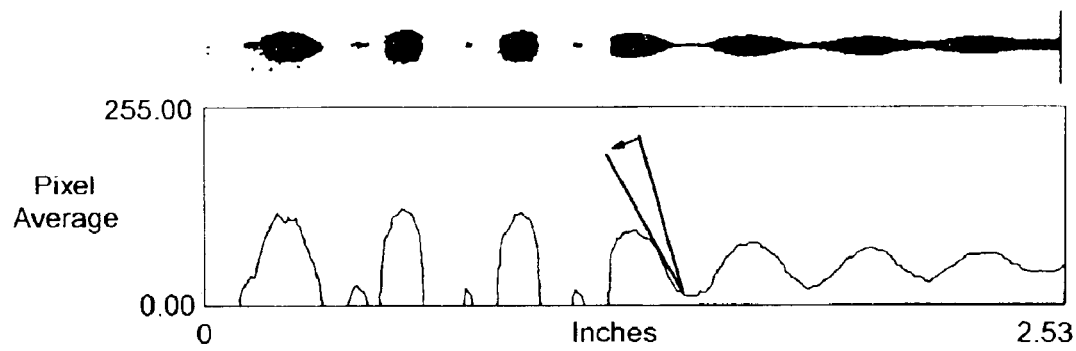
Figure 5C:
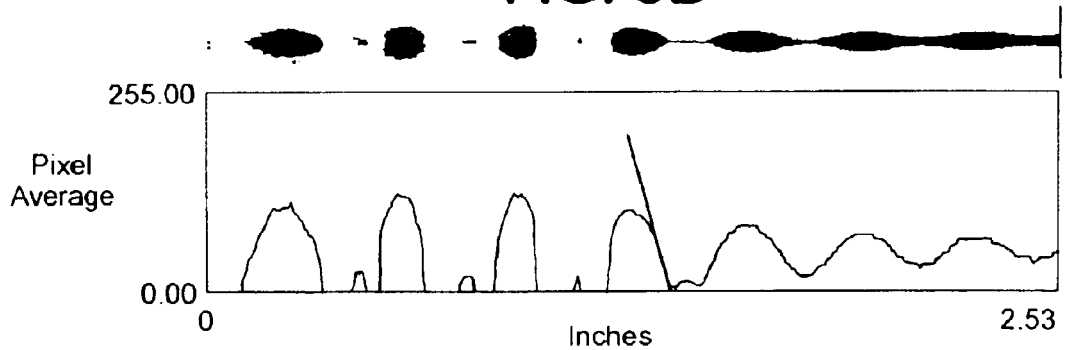
Figure 6:
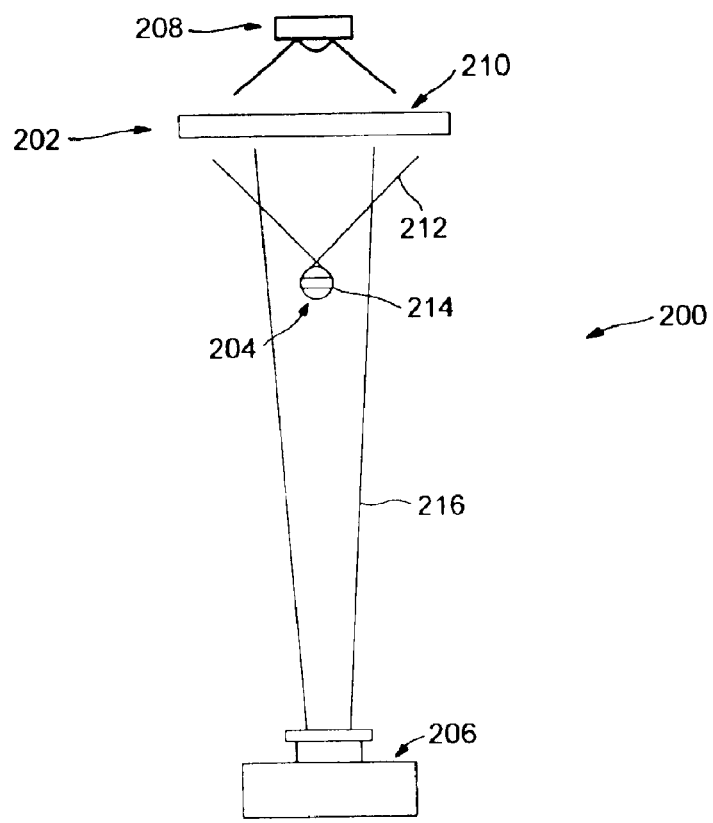
FIG. 6 is a plan view of an assembly for obtaining images of a jetting stream according to the prior art.

A determination was made that an increase in the crystal drive was necessary to restore the slope value to that of the reference FIG. 5A and the crystal drive was increased about 2.5%. Subsequent capture of multiple images after the increase in crystal drive and the generation of another sample histogram (FIG. 5C) and calculation of another sample slope average of 0.900, demonstrated that this method enabled restoration of the initial conditions and the stable sort of the reference standard.

All publications cited in this specification are incorporated herein by reference herein.

What is claimed is:

1. A method for sorting particles in a stream of a sample in a flow cytometer, comprising:
   (a) producing from a stable sort having desirable sort characteristics multiple images of a portion of said stream;
   (b) generating from said multiple images an averaged numerical reference standard representative of said stable sort;
   (c) continuously collecting during the sorting multiple running images of said portion of said stream;
   (d) generating from said multiple running images (c) at least one numerical sample average representative of the sample sort of each collection of said multiple running images, comprising the steps of:
      (1) converting said image (d) into a sample histogram having a downstream and upstream direction on the X axis, at least one neck region, and at least one undulation downstream of said neck region, said undulation comprising a positive slope nd a negative slope;
      (2) determining from each histogram a selected numerical value corresponding to the reference standard, wherein said numerical value is selected from the group consisting of:
         i. the slope of the upstream edge of an undulation appearing downstream of the neck region of each histogram;
         ii. the slope of the downstream edge of the undulation appearing upstream of the neck region of each histogram;
         iii. the average of the sum of the absolute values of the slopes (i) and (ii) for each histogram;
         iv. the midpoint of the segment defining the slope of the downstream undulation of each histogram;
         v. the integral of the area of the histogram between the lower of the slope values of slopes (i) and (ii); and
         vi. combinations thereof; and
      (3) averaging said selected numerical values from the multiple sample histograms of the multiple sample images (d) to create at least one numerical sample average of the sort of each collection of multiple running images; and
   (e) comparing each numerical sample average (d) to said numerical reference standard (b) and determining whether average (d) exhibits a deviation from said reference standard that requires an adjustment of said sort.

2. The method according to claim 1, further comprising the step of:
   (f) adjusting a processing condition of said sort in said cytometer as a function of said deviation.

3. The method according to claim 2, wherein said adjusting step (f) minimizes said deviation in subsequent sample averages and maintains the stable sort represented by said reference standard.

4. The method according to claim 2, wherein said adjusting step (f) stops said sort when said deviation causes a sample sort that is not correctable.

5. The method according to claim 1, wherein said multiple images (a) or (c) are multiple consecutive images.

6. The method according to claim 1, wherein said images (a) or (c) comprise images from which background noise is subtracted.

7. The method according to claim 1, wherein said generating step (b) comprises the steps of:
   converting each of said image (a) into a histogram having a downstream and upstream direction on the X axis, at least one neck region, and at least one undulation downstream of said neck region, said undulation comprising a positive slope and a negative slope;
   determining from each histogram a selected numerical value; and
   averaging said selected numerical values from the histogram of the multiple images to create said numerical reference standard.

8. The method according to claim 1, wherein said generating step (b) comprises the steps of:
   converting each multiple images (a) into a single average histogram having a downstream and upstream direction on the X axis, at least one neck region, and at least one undulation downstream of said neck region, said undulation comprising a positive slope and a negative slope;
   determining from said single average histogram a selected numerical sample average value to define said numerical reference standard.

9. The method according to claim 1, wherein said multiple images (a) or said series of consecutive multiple sample images (c) each comprise at least about 5 images.

10. The method according to claim 9, wherein said multiple images comprise about 5 to about 40 images.

11. The method according to claim 10, wherein said multiple images comprises about 10 to about 25 images.

12. The method according to claim 11, wherein said multiple images comprise about 10 images.

13. The method according to claim 1, wherein said portion of said stream is the droplet forming region formed after the stream exits a nozzle of said flow cytometer.

14. The method according to claim 13, wherein said portion of said stream comprises a proximal point wherein said stream exits said nozzle to a distal point at which the contiguous stream transitions into individual droplets.

15. The method according to claim 13, wherein said portion of said stream comprises the neck of said stream prior to the first drop that fully separates from said stream.

16. The method according to claim 1, further comprising applying one or more algorithms to said histogram to generate said numerical reference standard (b) and said numerical sample value (d).

17. The method according to claim 1, wherein said processing condition is selected from the group consisting of sheath pressure, sample pressure, crystal drive, crystal frequency, and a combination thereof.

18. The method according to claim 1, wherein said numerical value is selected from the group consisting of (i), (ii) and (iii) and the processing condition adjusted is crystal drive.

19. The method according to claim 1, wherein said numerical value is (iv), and said processing condition adjusted is the sheath pressure and sample pressure or crystal frequency.

20. The method according to claim 1, wherein said numerical value is (v), and said adjustment is ceasing the sort.

21. The method according to claim 1, wherein all or some of said steps are performed by a computer program.

22. The method according to claim 1, wherein said flow cytometer comprises:
   f) a device for serializing particles in said sample and a sheath fluid in a stream through a nozzle;
   g) a droplet generator for generating droplets from said stream; wherein said stream comprises a droplet-forming region;
   h) a detection device;
   i) a deflection device for charging said droplets so that the post-deflection trajectories of said droplets are a function of the charges;
   j) a collection device for collecting said droplets having common post-deflection trajectories; and
   k) a device for imaging a portion of said stream.

23. The method according to claim 1, further comprising the steps of:
   f) serializing particles in said sample and a sheath fluid in said stream;
   g) generating droplets from said stream; wherein said jetting stream segment exiting said nozzle contains a droplet-forming region;
   h) charging said droplets of said stream;
   i) deflecting said droplets so that the post-deflection trajectories of said droplets are a function of the charges; and
   j) collecting said droplets having common post-deflection trajectories.

24. A method for sorting particles in a stream of a sample in a flow cytometer, comprising:
   (a) producing from a stable sort having desirable sort characteristics multiple images of a portion of said stream, each said image of said stream by
      i. positioning said stream between an image capturing device and an illumination field, said illumination field comprising a light source and an opaque mask of a pre-determined pattern interposed between said light source and the stream, wherein said pre-determined pattern includes an elongate slit extending substantially parallel to the stream, and wherein said elongate slit has a width of about 3 to 30 times a width of the stream being imaged providing a pattern of contrasting light and dark areas, and
      ii. obtaining images of at least a portion of the stream backlit by said illumination field such that said images of the stream include an image of said pattern of contrasting light and dark areas as imaged within the fluid stream itself;
   (b) generating from said multiple images an averaged numerical reference standard representative of said stable sort;
   (c) continuously collecting during the sorting multiple series of consecutive images of the same portion of said stream;
   (d) generating from each said multiple series of consecutive images (c) at least one numerical sample average representative of the sample sort of each collection of said multiple running images; and
   (e) comparing each numerical sample average (d) to said numerical reference standard (b) and determining whether average (d) exhibits a deviation from said reference standard that requires an adjustment of said sort,
   wherein said process continually corrects for any said deviation.

25. The method according to claim 24, wherein said pre-determined pattern farther comprises one or more distinguishing marks that appear as reference marks on said image.

26. A method for sorting particles in a stream of a sample in a flow cytometer, comprising:
   (a) producing from a stable sort having desirable sort characteristics multiple images of a portion of said stream, each image of said stream being captured by
      i. positioning said stream between an image capturing device and an illumination field, said illumination field having a pattern of contrasting light and dark areas, and said image capturing device having an angle of light acceptance that captures a full width of the stream and light from said illumination field projecting externally and adjacent the lateral edges of the stream; and
      ii. obtaining images of at least a portion of the stream backlit by said illumination field such that said images of the stream include an image of said pattern of contrasting light and dark areas as imaged within the fluid stream itself, wherein said dark areas mark the lateral edges of the stream as seen in said images, and
   (b) generating from said multiple images an averaged numerical reference standard representative of said stable sort;
   (c) continuously collecting during the sorting multiple series of consecutive images of the same portion of said stream;
   (d) generating from each said multiple series of consecutive images (c) at least one numerical sample average representative of the sample sort of each collection of said multiple running images; and
   (e) comparing each numerical sample average (d) to said numerical reference standard (b) and determining whether average (d) exhibits a deviation from said reference standard that requires an adjustment of said sort,
   wherein said process continually corrects for any said deviation.

27. A method for sorting particles in a stream of a sample in a flow cytometer, comprising:
   (a) producing from a stable sort having desirable sort characteristics multiple images of a portion of said stream;
   (b) generating from said multiple images an averaged numerical reference standard representative of said stable sort;
   (c) continuously collecting during the sorting multiple running images of said portion of said stream;
   (d) generating from said multiple running images (c) at least one numerical sample average representative of the sample sort of each collection of said multiple running images; and
   e) comparing each numerical sample average (d) to said numerical reference standard (b) and determining whether average (d) exhibits a deviation from said reference standard that requires an adjustment of said sort, wherein said numerical reference standard and said numerical sample average are selected from the group consisting of:
    i. the averaged slope of the upscam edge of an undulation appearing downstream of the neck region of histograms generated from each multiple of images (a) or (c);
    ii. the averaged slope of the downstream edge of the undulation appearing upstream of the neck region of said histograms;
    iii. the average of the sum of the absolute values of the slopes (i) and (ii) for said histograms;
    iv. the averaged midpoint of the segment defining the slope of the downstream undulation of said histograms;
    v. the averaged integral of the area of said histograms between the lower of the slope valves of slopes (i) and (ii); and
    vi. combinations thereof.

28. A system for storing particles in a stream of a sample in a flow cytometer comprising:
    a) an imaging means for producing multiple images of a portion of said stream; and
    b) at least one information processing device for
        i. generating from multiple images of a stable sort having desirable characteristics an averaged numerical reference standard representative of said stable sort;
        ii. continuously collecting during the sorting multiple running images of said portion of said stream and generating from said multiple running images at least one numerical sample average representative of the sample sort of each collection of said multiple running images; and
        iii. comparing each numerical sample average to said numerical reference standard and determining whether any of said sample averages exhibits a deviation from said reference standard requiring an adjustment to said sort;
wherein said device (b) converts said multiple images of said stable sort into a single average histogram having a downstream and upstream direction of the X axis, at least one neck region, and at least one undulation downstream of said neck region, said undulation comprising a positive slope and a negative slope; determines from each histogram a selected numerical value corresponding to the reference standard; and averages said selected numerical values from the multiple sample histograms of the multiple sample images to create at least one numerical sample average of the sample sort of each collection of multiple running images,
wherein said numerical value is selected from the group consisting of:
    iv. the slope of the upstream edge of an undulation appearing downstream of the neck region of each histogram;
    v. the slope of the downstream edge of the undulation appearing upstream of the neck region of each histogram;
    vi. the average of the sum of the absolute values of the slopes (iv) and (v) for each histogram;
    vii. the midpoint of the segment defining the slope of the downstream undulation of each histogram;
    viii. the integral of the area of the histogram between the lower of the slope values of slopes (iv) and (v); and
    ix. combinations thereof.

29. The system according to claim 28, further comprising
    c) means for adjusting a processing condition of said sort in said cytometer as a function of said deviation, to minimize said deviation in subsequent sample averages to maintain the stable sort of said reference standard.

30. The system according to claim 29, wherein said adjusting means adjusts a processing condition selected from the group consisting of sheath and sample pressure, crystal drive, crystal frequency, and a combination thereof.

31. The system according to claim 28, wherein said multiple images are multiple consecutive images.

32. The system according to claim 28, wherein said images comprise images from which background noise is subtracted.

33. The system according to claim 28, wherein said device (b) converts each said image of said stable sort into a histogram having a downstream and upstream direction on the X axis, at least one neck region, and at least one undulation downstream of said neck region, said undulation comprising a positive slope and a negative slope; determines from each histogram a selected numerical value; and averages said selected numerical values from the histograms of the multiple images to create said numerical reference standard.

34. The system according to claim 33, wherein said device (b) applies at least one algorithm to said histogram of said stable sort images to generate said numerical reference standard.

35. The system according to claim 28, wherein said device (b) converts said multiple images of said stable sort into a single average histogram having a downstream and upstream direction on the X axis, at least one neck region, and at least one undulation downstream of said neck region, said undulation comprising a positive slope and a negative slope; and determines from said single average histogram a selected numerical average value to define said numerical reference standard.

36. The system according to claim 28, wherein said device (b) converts said multiple series of consecutive sample images into a single average sample histogram having a downstream and upstream direction on the X axis, at least one neck region, and at least one undulation downstream of said neck region, said undulation comprising a positive slope and a negative slope; and determines from said single average sample histogram a selected numerical sample average value of the sample sort of each collection of multiple series of consecutive images.

37. The system according to claim 28, wherein said means for adjusting minimizes said deviation in subsequent sample averages and maintains the stable sort represented by said reference standard.

38. The system according to claim 28, wherein said means for adjusting comprises means for stopping said sort when said deviation causes a sample sort that cannot be corrected.

39. The system according to claim 28, wherein said multiple stable sort images or said multiple series of consecutive sample images each comprise at least about 5 images.

40. The system according to claim 39, wherein said multiple images comprise about 5 to about 40 images.

41. The system according to claim 39, wherein said multiple images comprise about 10 images.

42. The system according to claim 28, wherein said portion of said stream is the droplet forming region formed after the stream exits a nozzle of said flow cytometer.

43. The system according to claim 42, wherein said portion of said stream, comprises a proximal point wherein said stream exits said nozzle to a distal point at which the contiguous stream transitions into individual droplets.

44. The system according to claim 43, wherein said portion of said stream comprises the neck of said stream prior to the first drop that fully separates from said stream.

45. The system according to claim 28, wherein said device (b) uses at least one algorithm applied to said sample average histogram to generate said numerical sample average.

46. The system according to claim 28, wherein said numerical value is selected from the group consisting of (iv), (v), and (vi) and the processing condition adjusted is crystal drive.

47. The system according to claim 28, wherein said numerical value is (vii), and said processing condition adjusted is the sheath pressure, and further wherein said adjusting means adjusts sample pressure with said sheath pressure or crystal frequency.

48. The system according to claim 28, wherein said numerical value is (viii), and said adjusting means stops the sort.

49. The system according to claim 28, wherein all or some of said means are computer-assisted.

50. The system according to claim 28, further comprising:
   c) a flow device for serializing particles in said sample and a sheath fluid in a stream through a nozzle;
   d) a droplet generator for generating droplets from said stream; wherein said stream comprises a droplet-forming region;
   e) a detection device;
   f) a charging device for charging said droplets;
   g) a deflection device for generating post-deflection trajectories of said droplets that are a function of the charges; and
   h) a collection device for collecting said droplets having common post-deflection trajectories.

51. A system for sorting particles in a stream of a sample in a flow cytometer comprising:
   a) an imaging means for producing multiple images of a portion of said stream;
   b) an illumination field comprising a light source and an opaque mask of a pre-determined pattern of light and dark areas interposed between said light source and the stream, wherein said pre-determined pattern includes an elongate slit extending substantially parallel to the stream, and wherein said elongate slit has a width of about 3 to 30 times a width of the stream being imaged, and wherein said imaging means is positioned to obtain images of at least a portion of the stream backlit by said illumination field such that said images of the stream include an image of said pattern of contrasting light and dark areas as imaged within the fluid stream itself; and
   c) at least one information processing device for
      i. generating from multiple images of a stable sort having desirable characteristics an averaged numerical reference standard representative of said stable sort;
      ii. continuously collecting during the sorting multiple series of consecutive images of said portion of said stream and generating from said multiple series of consecutive images at least one numerical sample average representative of the sample sort of each collection of said multiple series of consecutive images; and
      iii. comparing each numerical sample average to said numerical reference standard and determining whether any of said sample averages exhibits a deviation from said reference standard requiring an adjustment to said sort, wherein said system continually corrects for any said deviation.

52. The system according to claim 51, wherein said pre-determined pattern further comprises one or more distinguishing marks that appear as reference marks on said image.

53. A system for sorting particles in a stream of a sample in a flow cytometer comprising:
   a) an imaging means for producing multiple images of a portion of said stream;
   b) an illumination field having a pattern of contrasting light and dark areas, and wherein said imaging means is positioned to obtain images of at least a portion of the stream backlit by said illumination field such that said images of the stream include an image of said pattern of contrasting light and dark areas as imaged within the fluid stream itself, wherein said dark areas mark the lateral edges of the stream as seen by said imaging means, and wherein said imaging means has an angle of light acceptance that captures a full width of the stream and light from said illumination field projecting externally and adjacent the lateral edges of the stream; and
   c) at least one information processing device for
      i. generating from multiple images of a stable sort having desirable characteristics an averaged numerical reference standard representative of said stable sort;
      ii. continuously collecting during the sorting multiple series of consecutive images of said portion of said stream and generating from said multiple series of consecutive images at least one numerical sample average representative of the sample sort of each collection of said multiple series of consecutive images; and
      iii. comparing each numerical sample average to said numerical reference standard and determining whether any of said sample averages exhibits a deviation from said reference standard requiring an adjustment to said sort, wherein said system continually corrects for any said deviation.

54. A flow cytometer for sorting particles in a fluid stream, comprising:
   a) an illumination field comprising
      i. a light that comprises Light emitting diodes; and
      ii. an opaque mask of a pre-determined geometric pattern of contrasting light and dark areas, wherein said mask consists of a single elongate slit defining said geometric pattern and extends substantially parallel to the fluid stream being imaged, said mask interposed between said light source and the fluid stream, said illumination field positioned relative to said fluid stream for illuminating the fluid stream from a side thereof, said illumination field providing a pattern of contrasting light and dark areas; and
   b) an image capturing device positioned to obtain an image of at least a portion of the fluid stream backlit by said illumination field such that said image of the fluid stream captured by said image capturing device includes said pattern of contrasting light and dark areas imaged within the stream acting as a lens, said dark areas marking the lateral edges of the fluid stream, wherein said image of said stream is improved in contrast, permitting more control of said sorting.

55. The flow cytometer according to claim 54, wherein said elongate slit has a width of about 3 to 30 times a width of the fluid stream being imaged.

56. The flow cytometer according to claim 54, wherein said image capturing device has an angle of light acceptance that captures a full width of the fluid stream and light from said light source projecting externally and adjacent the lateral edges of the fluid stream.

57. A flow cytometer for sorting particles in a fluid stream, comprising:
  a) an illumination field comprising
    i. a light source that comprises light emitting diodes; and
    ii. an opaque mask of a pre-determined geometric pattern of contrasting light and dark areas interposed between said light source and the fluid stream, wherein said geometric pattern includes at least one distinguishing mark that appears as a reference mark within said image of the fluid stream, and wherein said field is positioned relative to said fluid stream for illuminating the fluid stream from a side thereof; and
  b) an image capturing device positioned to obtain an image of at least a portion of the fluid stream backlit by said illumination field such that said image of the fluid stream captured by said image capturing device includes said pattern of contrasting light and dark areas imaged within the stream acting as a lens, wherein said image of said stream is improved in contrast, permitting more control of said sorting.

* * * * *